(12) United States Patent
Learmonth et al.

(10) Patent No.: US 9,446,012 B2
(45) Date of Patent: Sep. 20, 2016

(54) PHARMACEUTICAL COMPOUNDS

(71) Applicant: BIAL-PORTELA & CA, S.A., S. Mamede do Coronado (PT)

(72) Inventors: David Alexander Learmonth, Valongo (PT); Laszlo Erno Kiss, Lavra (PT); Pedro Nuno Leal Palma, Leca Da Palmeira (PT); Humberto dos Santos Ferreira, Maia (PT); Patricio Manuel V. A. Soares da Silva, Porto (PT)

(73) Assignee: BIAL—PORTELA & CA, S.A., S. Mamede Do Coronado (PT)

( * ) Notice: Subject to any disclaimer, the term of this patent is extended or adjusted under 35 U.S.C. 154(b) by 0 days.

(21) Appl. No.: 14/014,548

(22) Filed: Aug. 30, 2013

(65) Prior Publication Data

US 2014/0024682 A1 Jan. 23, 2014

Related U.S. Application Data

(63) Continuation of application No. 12/226,260, filed as application No. PCT/PT2007/000016 on Apr. 10, 2007, now Pat. No. 8,536,203.

(30) Foreign Application Priority Data

Apr. 10, 2006 (EP) .................................... 06007534

(51) Int. Cl.
*A61K 31/44* (2006.01)
*C07D 413/04* (2006.01)
(Continued)

(52) U.S. Cl.
CPC .......... *A61K 31/198* (2013.01); *A61K 31/4439* (2013.01); *C07D 213/26* (2013.01);
(Continued)

(58) Field of Classification Search
CPC .............. C07D 413/04; C07D 213/61; A61K 31/4439
USPC ................................ 514/340; 546/269.4, 332
See application file for complete search history.

(56) References Cited

U.S. PATENT DOCUMENTS

| 1,532,178 A | 4/1925 | Godbold, Louis |
| 3,647,809 A | 3/1972 | Reiter et al. |

(Continued)

FOREIGN PATENT DOCUMENTS

| CN | 1340500 | 3/2002 |
| CN | 1173926 | 11/2004 |

(Continued)

OTHER PUBLICATIONS

Dmitriyeva et al. "Features of the reaction of some 2-chloronicotinonitriles with hydroxylamine. Synthesis of 3-(1, 2, 4-oxadiazol-3yl)pyridines and their fragmentation under electron impact." IzvestiyaVysshikh UchehnykhZavedenii, Khimiya i Khimicheskaya Tekhnologiya, 2005, vol. 48, No. 11, pp. 15-17, CAPLUS Abstract, DN 145:103612.*

(Continued)

*Primary Examiner* — Shengjun Wang
(74) *Attorney, Agent, or Firm* — McCarter & English, LLP; Steven G. Davis; Wei Song

(57) ABSTRACT

This invention relates to novel substituted nitrocatechol derivatives, their use in the treatment of some central and peripheral nervous system disorders and pharmaceutical compositions containing them.

14 Claims, 3 Drawing Sheets

Figure 1:
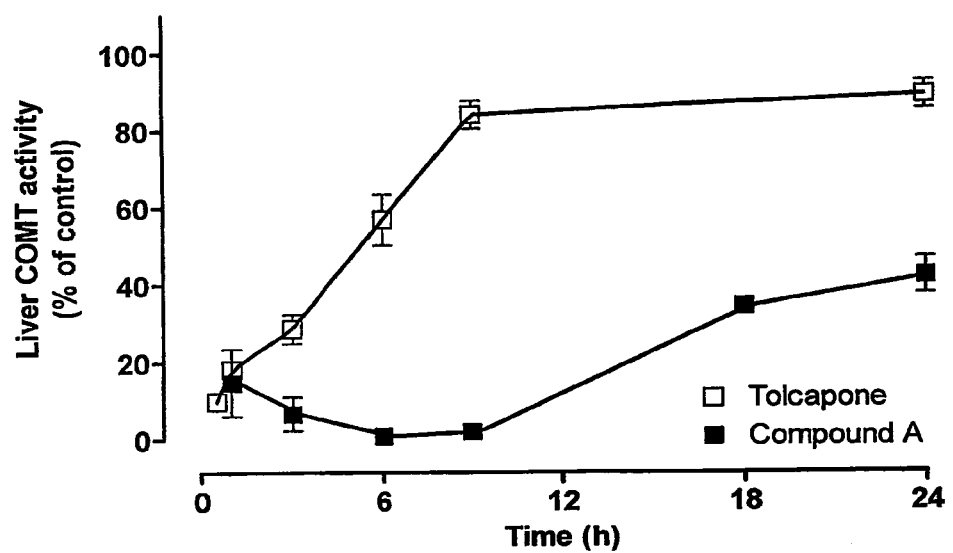

(51) Int. Cl.
| | |
|---|---|
| C07D 213/00 | (2006.01) |
| A61K 31/198 | (2006.01) |
| C07D 213/26 | (2006.01) |
| C07D 213/57 | (2006.01) |
| C07D 401/04 | (2006.01) |
| C07D 407/04 | (2006.01) |
| C07D 417/04 | (2006.01) |
| A61K 31/4439 | (2006.01) |
| C07D 213/82 | (2006.01) |

(52) U.S. Cl.
CPC .......... *C07D213/57* (2013.01); *C07D 213/82* (2013.01); *C07D 401/04* (2013.01); *C07D 407/04* (2013.01); *C07D 413/04* (2013.01); *C07D 417/04* (2013.01)

(56) References Cited

U.S. PATENT DOCUMENTS

| | | | |
|---|---|---|---|
| 4,065,563 A | 12/1977 | Narayanan et al. | |
| 4,264,573 A | 4/1981 | Powell et al. | |
| 4,386,668 A | 6/1983 | Parish | |
| 4,963,590 A | 10/1990 | Backstrom et al. | |
| 5,236,952 A | 8/1993 | Bernauer et al. | |
| 5,476,875 A | 12/1995 | Bernauer et al. | |
| 5,633,371 A * | 5/1997 | Bernauer et al. | 544/105 |
| 5,705,703 A | 1/1998 | Bernauer et al. | |
| 5,840,769 A | 11/1998 | Kolter et al. | |
| 6,206,110 B1 | 3/2001 | Slaughter et al. | |
| 6,500,867 B1 | 12/2002 | Virkki et al. | |
| 6,509,363 B2 | 1/2003 | Salituro et al. | |
| 6,512,136 B1 | 1/2003 | Benes et al. | |
| 6,660,753 B2 | 12/2003 | Van Wagenen et al. | |
| 7,041,685 B2 | 5/2006 | Cai et al. | |
| 7,112,595 B2 | 9/2006 | Wagenen et al. | |
| 7,144,876 B2 | 12/2006 | Cai et al. | |
| 7,317,029 B2 | 1/2008 | Cai et al. | |
| 7,435,750 B2 | 10/2008 | Cai et al. | |
| 7,553,964 B2 | 6/2009 | Liu et al. | |
| 8,168,793 B2 | 5/2012 | Learmonth et al. | |
| 8,524,746 B2 | 9/2013 | Learmonth et al. | |
| 8,536,203 B2 | 9/2013 | Learmonth et al. | |
| 8,907,099 B2 | 12/2014 | Learmonth et al. | |
| 9,126,988 B2 | 9/2015 | Russo et al. | |
| 2002/0012701 A1 | 1/2002 | Kolter et al. | |
| 2003/0055085 A1 | 3/2003 | Wagenen et al. | |
| 2004/0097555 A1 | 5/2004 | Ohkawa et al. | |
| 2004/0138281 A1* | 7/2004 | Wikstrom et al. | 514/410 |
| 2004/0171645 A1* | 9/2004 | Bartoszyk et al. | 514/337 |
| 2006/0019956 A1 | 1/2006 | Green | |
| 2006/0160812 A1 | 7/2006 | Schubert et al. | |
| 2006/0173074 A1 | 8/2006 | Ellmen et al. | |
| 2006/0257473 A1 | 11/2006 | Puranajoti | |
| 2007/0013830 A1 | 1/2007 | Hayakawa | |
| 2007/0026054 A1 | 2/2007 | Theobald et al. | |
| 2007/0048384 A1 | 3/2007 | Rosenberg et al. | |
| 2007/0078133 A1 | 4/2007 | Liu et al. | |
| 2007/0117165 A1 | 5/2007 | Presnell et al. | |
| 2007/0219187 A1 | 9/2007 | Bessis et al. | |
| 2007/0299110 A1 | 12/2007 | Gagliardi et al. | |
| 2008/0051441 A1 | 2/2008 | Brown et al. | |
| 2008/0071184 A1 | 3/2008 | Carter | |
| 2008/0167286 A1 | 7/2008 | Gopalakrishnan et al. | |
| 2008/0269236 A1 | 10/2008 | Ji et al. | |
| 2009/0000437 A1 | 1/2009 | Johnson et al. | |
| 2009/0054437 A1 | 2/2009 | Learmonth et al. | |
| 2009/0111778 A1 | 4/2009 | Apodaca et al. | |
| 2009/0162283 A1 | 6/2009 | Bando et al. | |
| 2009/0227626 A1 | 9/2009 | Deraeve et al. | |
| 2009/0312347 A1 | 12/2009 | Dahl et al. | |
| 2010/0004284 A1 | 1/2010 | Farina et al. | |
| 2010/0113529 A1 | 5/2010 | Learmonth et al. | |
| 2010/0168113 A1 | 7/2010 | Learmonth et al. | |
| 2010/0256193 A1 | 10/2010 | Cardoso de Vasconcelos et al. | |
| 2010/0256194 A1 | 10/2010 | Cardoso de Vasconcelos et al. | |
| 2011/0014282 A1 | 1/2011 | de Vasconcelos | |
| 2011/0112301 A1 | 5/2011 | Learmonth et al. | |
| 2011/0301204 A1 | 12/2011 | de Almeida et al. | |
| 2012/0196904 A1 | 8/2012 | Learmonth et al. | |
| 2013/0324578 A1 | 12/2013 | Soares Da Silva et al. | |
| 2013/0331416 A1 | 12/2013 | Learmonth et al. | |
| 2014/0045900 A1 | 2/2014 | Soares Da Silva et al. | |
| 2014/0350057 A1 | 11/2014 | Russo et al. | |
| 2015/0072977 A1 | 3/2015 | Learmonth et al. | |
| 2015/0166519 A1 | 6/2015 | Learmonth | |
| 2015/0359783 A1 | 12/2015 | de Vasconcelos et al. | |
| 2016/0009699 A1 | 1/2016 | Learmonth et al. | |
| 2016/0009700 A1 | 1/2016 | Russo et al. | |

FOREIGN PATENT DOCUMENTS

| | | |
|---|---|---|
| DE | 37 40 383 | 6/1988 |
| EP | 0237929 A1 | 9/1987 |
| EP | 0372654 A2 | 6/1990 |
| EP | 0487774 | 11/1990 |
| EP | 0462639 A1 | 12/1991 |
| EP | 1 167 342 | 1/2002 |
| EP | 1 845 097 | 10/2007 |
| EP | 1 881 979 | 8/2010 |
| FR | 1260080 | 5/1961 |
| JP | H10-67651 A | 3/1998 |
| JP | 2002-020319 A | 1/2002 |
| JP | 2003-116966 A | 4/2003 |
| WO | 93/13083 A1 | 7/1993 |
| WO | WO-00/37423 | 6/2000 |
| WO | WO-01/12627 | 2/2001 |
| WO | 01/68083 A1 | 9/2001 |
| WO | WO-02/17175 | 2/2002 |
| WO | 02/051442 A1 | 7/2002 |
| WO | WO-02/068417 | 9/2002 |
| WO | 02/096867 A2 | 12/2002 |
| WO | 02/100826 A2 | 12/2002 |
| WO | WO-2005/013982 | 2/2005 |
| WO | WO-2005/044797 | 5/2005 |
| WO | 2005/105780 A2 | 11/2005 |
| WO | 2006/061697 A1 | 6/2006 |
| WO | 2006/071184 A1 | 7/2006 |
| WO | WO-2006/114400 | 11/2006 |
| WO | WO-2006/129199 | 12/2006 |
| WO | WO-2006/132914 | 12/2006 |
| WO | WO-2007/013830 | 2/2007 |
| WO | WO-2007/113276 | 10/2007 |
| WO | WO-2007/117165 | 10/2007 |
| WO | WO-2008/021388 | 2/2008 |
| WO | WO-2008/094053 | 8/2008 |
| WO | WO-2009/029632 | 3/2009 |
| WO | 2010/014025 A1 | 2/2010 |
| WO | 2011/107653 A2 | 9/2011 |
| WO | 2012/107708 A1 | 8/2012 |

OTHER PUBLICATIONS

Database Caplus [Online], Chemical Abstracts Service, Columbus, Ohio, US XP002440393, retrieved from STN accession No. 2003:365244, Database accession No. 138:337989, Abstract.
EPO Search Report and Written Opinion for EPO Pat. Appln. No. 06075343, dated Mar. 28, 2006.
International Preliminary Report on Patentability for Intl. Pat. Appln. No. PCT/PT2007/000016, dated Oct. 14, 2008.
International Search Report and Written Opinion for Intl. Pat. Appln. No. PCT/PT2007/000016, mailed on Jul. 13, 2007.
Nutt, J.G., "Catechol-O-methyltransferase inhibitors for treatment of Parkinson's disease", *The Lancet*, (Apr. 1998), Commentary, vol. 351, pp. 1221-1222.
Nutt, J.G., et al., "Pharmacokinetics of Levodopa", *Clin. Neuropharmacol*, (1984), vol. 7, No. 1, pp. 35-49, Raven Press.
Parashos, S.A. et al., "Frequency, Reasons, and Risk Factors in Entacapone Discontinuation in Parkinson Disease," *Clin. Neuropharmacol*, (Jun. 2004), vol. 27, No. 3, pp. 119-123.
Pedrosa, R. et al., "Oxidative and non-oxidative mechanisms of neuronal cell death and apoptosis by L-3, 4-dihydroxyphenylalanine ($_L$-DOPA) and dopamine", *British Journal of Pharmacology*, (2002), vol. 137 (8), pp. 1305-1313, Nature Publishing Group.

(56) References Cited

OTHER PUBLICATIONS

Poulain, R. F. et al., "Parallel synthesis of 1,2,4-oxadiazoles from carboxylic acids using an improved, uronium-based, activation," Tetrahedron Letters 42:1495-1498 (2001).

Reches, A. et al., "3-O-Methyldopa inhibits rotations induced by levodopa in rats after unilateral destruction of the nigrostriatal pathway," *Neurology*, (Aug. 1982), 32, pp. 887-888.

Smith, K.S. et al., "In Vitro Metabolism of Tolcapone to Reactive Intermediates: Relevance to Tolcapone Liver Toxicity," *Chem. Res. Toxicol.*, (2003), vol. 16, No. 2, pp. 123-128.

Soares-da-Silva, P. et al., The O-methylated derivative of $_L$-DOPA, 3-O-methyl-$^L$-DOPA, fails to inhibit neuronal and non-neuronal aromatic L-amino acid decarboxylase, *Brain Research*, (2000), 863, pp. 293-297.

Tohgi, H. et al., "The significance of 3-O-methyldopa concentrations in the cerebrospinal fluid in the pathogenesis of wearing-off phenomenon in Parkinson's disease," *Neuroscience Letters*, (1992), 132, pp. 19-22.

Vieira-Coelho, M. A et al., "Effects of tolcapone upon soluble and membrane-bound brain and liver catechol-O-methyltransferase," *Brain Research*, (1999) 821, pp. 69-78.

[No Author Listed] "[1,2,4]-oxadazolyl nitrocatechol derivatives" ip.com Journal, ip.com Inc., West Henrietta, NY, US, May 3, 2012. XP013150541.

[No Author Listed] COMT inhibitor definition from Wikipedia, retrieved from http://en.wikipedia.org/w/index.php?title=COMT_inhibitor&oldid=478541384, last accessed Jan. 31, 2014.

Al-Mousawi, S.M. et al., "Alkylazinylcarbonitriles as building blocks in heterocyclic synthesis: a route for the synthesis of 4-methyl-2-oxopyridines," Pharmazie, 54, 8, pp. 571-574 (1999).

Al-Omran, F. et al., "Heterocyclic Synthesis via Enaminones: Novel Synthesis of (1 H)-Pyridin-2-one, Pyrazolo [1,5-?]pyrimidine and Isoxazole Derivatives Incorporating a N-Methylphthalimide and Their Biological Evaluation", J. Heterocyclic Chem., 42, pp. 307-312 (2005).

Ansel et al., Pharmaceutical Dosage Forms and Drug Delivery Systems, 6th edition, 1995. pp. 192-203.

Bondvalli et al., "An Efficient Synthesis of Functionalized 2-Pyridones by Direct Route or via Amide/Enolate Ammonium Salt Intermediates", Synthesis, No. 7, pp. 1169-1174 (1999).

Davies, Ian W. et al., "A General [3 + 2 + 1] Annulation Strategy for the Preparation of Pyridine N-Oxides", Organic Letters, vol. 3, No. 2, pp. 209-211 (2001).

English translation of JP 2003-116966.

Girges et al., (Chemical Papers (1992), 46(4), 272-277).

Grosset, D.G. et al., Parkinson's Disease, Clinician's Desk Reference, Manson Publishing, 2009, p. 62.

Howse, "Brocresine in Parkinson's disease, Action of a peripheral and central decarboxylase inhibitor in potentiating levodopa," Journal of Neurology, Neurosurgery, and Psychiatry, 1973, 36, pp. 27-29.

International Preliminary Report on Patentability for PCT/PT2006/000020, mailed Jan. 29, 2008.

International Preliminary Report on Patentability for PCT/PT2007/000043, mailed Aug. 4, 2009.

International Preliminary Report on Patentability for PCT/PT2009/000044, mailed Feb. 10, 2011.

International Search Report and Written Opinion for PCT/PT2006/000020, mailed Nov. 8, 2006.

International Search Report and Written Opinion for PCT/PT2007/000043, mail date Apr. 23, 2008.

International Search Report and Written Opinion for PCT/PT2009/000044, mail date Nov. 16, 2009, 16 pages.

Ivanova, L.A., "Technology of dosage forms," Moscow, Medicine, vol. 2, 1991, pp. 223-224. English translation.

Kiss, L. E. et al., "Discovery of a long-acting, peripherally selective inhibitor of a catechol-O-methyltransferase" Journal of Medicinal Chemistry, American Chemical Society, US, vol. 53, No. 8, Apr. 22, 2010, pp. 3396-3411. XP002594266.

Korolkovas, A. "Essentials of Medicinal Chemistry", Development of Drugs, Second Edition, pp. 97-103 and 135-137 (1988).

Kristensen et al., "Granulation A Review on Pharmaceutical Wet-Granulation Drug Development and Industrial Pharmacy", 13(4 &5), 803-872 (1987).

Krogsgaard-Larsen, P. et al., "Textbook of Drug Design and Discovery", Third Edition, Table 14.3, pp. 426-427 (2002).

Learmonth, David., et al., "Chemical Synthesis and Characterization of Conjugates of a Novel Catechol-O-methyltransferase Inhibitor", Bioconjugate Chem., vol. 13, pp. 1112-1118, American Chemical Society, 2002.

Marcoux, Jean-Francois et al., "A General Preparation of Pyridines and Pyridones via the Annulation of Ketones and Esters," J. Org. Chem, 66, pp. 4194-4199 (2001).

Morbus Parkinson, Stellenwert von COMT-Hemmern Bestatigt, May 3, 2004, 2 pages.

Rasenack, N et al., "Micron-size drug particles: common and novel micronization techniques", Pharmaceutical Development and Technology, New York, NY, US, vol. 9, No. 1., Jan. 1, 2004, pp. 1-13. XP009055393.

Tervo, Anu J., et al., "A structure-activity relationship study of catechol-O-methyltransferase inhibitors combining molecular docking and 3D QSAR methods", Journal of Computer-Aided Molecular Design, vol. 17, pp. 797-810, Kluwer Academic Publishers, 2003.

\* cited by examiner

PHARMACEUTICAL COMPOUNDS

This application is a continuation of U.S. patent application Ser. No. 12/226,260, filed Oct. 10, 2008 and now U.S. Pat. No. 8,536,203, which is a 35 U.S.C. §371 national stage filing of International Application No. PCT/PT2007/000016, filed Apr. 10, 2007, which, in turn, claims priority under 35 U.S.C. §119 or 365 to European Application No. 06007534.8, filed Apr. 10, 2006. The entire contents of each of the aforementioned applications are incorporated herein by reference.

This invention relates to novel substituted nitrocatechol derivatives, their use in the treatment of some central and peripheral nervous system disorders and pharmaceutical compositions containing them.

Despite being used in clinical practice for several decades, levodopa (L-DOPA) continues to be the gold standard drug for the symptomatic treatment of Parkinson's disease. This has helped to maintain keen interest in the development of inhibitors of the enzyme catechol-O-methyltransferase (COMT) based on the hypothesis that inhibition of this enzyme may provide clinical improvements in patients afflicted by Parkinson's disease undergoing treatment with L-DOPA and a peripheral amino acid decarboxylase (AADC) inhibitor.

The rationale for the use of COMT inhibitors as adjuncts to L-DOPA/AADC therapy is based on their ability to reduce metabolic O-methylation of L-DOPA to 3-O-methyl-L-DOPA (3-OMD). The duration of L-DOPA induced clinical improvement is brief as a result of the short in vivo half-life of L-DOPA which contrasts with the long half-life of 3-OMD. Additionally, 3-OMD competes with L-DOPA for transport across the blood-brain bather (BBB), which means that only a very limited amount of an orally administered dose of L-DOPA actually reaches the site of action, i.e. the brain. Commonly, within only a few years of starting L-DOPA therapy with the usual dosage regime, L-DOPA induced clinical improvement declines at the end of each dose cycle, giving rise to the so-called 'wearing-off' pattern of motor fluctuations. A close relationship between the 'wearing-off' phenomenon and accumulation of 3-OMD has been described (Tohgi, H., et al., Neurosci. Letters, 132:19-22, 1992). It has been speculated that this may result from impaired brain penetration of L-DOPA due to competition for the transport system across the BBB with 3-OMD (Reches, A. et al., Neurology, 32:887-888, 1982) or more simply that there is less L-DOPA available to reach the brain (Nutt, J. G., Fellman, J. H., Clin. Neuropharmacol., 7:35-49, 1984). In effect, COMT inhibition protects L-DOPA from metabolic breakdown in the periphery through O-methylation, such that with repeated doses of L-DOPA, the mean plasma L-DOPA concentration is raised. In addition to reduced competition for transport into the brain, a significantly greater percentage of the orally administered dose of L-DOPA is able to reach the site of action. Thus COMT inhibition serves to increase the bioavailability of L-DOPA and the duration of antiparkinsonian action is prolonged with single doses of L-DOPA (Nutt, J. G., Lancet, 351:1221-1222, 1998).

The most potent COMT inhibitors thusfar reported are 3,4-dihydroxy-4'-methyl-5-nitrobenzophenone (Tolcapone, Australian pat. AU-B-69764/87) and (E)-2-cyano-N,N-diethyl-3-(3,4-dihydroxy-5-nitrophenyl)acrylamide (Entacapone, German pat. DE 3740383 A1) which all have inhibition constants in the low nanomolar range. Although sharing essentially the same pharmacophore, tolcapone differs from entacapone in that it easily enters the central nervous systems (CNS) and is able to inhibit cerebral COMT as well as peripheral COMT. It could be speculated that central inhibition may be less important if the more significant action of inhibiting COMT is to prevent breakdown of L-DOPA in the periphery. Indeed, the use of COMT inhibitors which do not penetrate into the brain at clinically relevant doses may avoid potentially undesirable CNS side-effects of these agents.

Another serious issue which has emerged since these COMT inhibitors were introduced into clinical practice relates to the potential of these nitrocatechol-based xenobiotics to cause severe liver damage (hepatotoxicity). Indeed, shortly after its launch, tolcapone was withdrawn from the market after several cases of hepatotoxicity were reported including three unfortunate deaths from fatal fulminant hepatitis. Today tolcapone can only be used in Parkinsonian patients who are unresponsive to other treatments and strictly only with regular monitoring of liver function, which is expensive and inconvenient for the patient. Although the actual mechanistic causes of the liver toxicity associated with tolcapone are not fully understood, in vitro studies have shown that tolcapone may be reduced metabolically to reactive intermediates and it has been speculated that these may form covalent adducts with hepatic proteins resulting in hepatocellular injury (Smith, K. S. et al, Chem. Res. Toxicol., 16:123-128, 2003). Entacapone on the other hand, although sharing the same nitrocatechol pharmacophore with tolcapone, is not associated with liver toxicity and is generally regarded as a safe drug. Unfortunately however, entacapone is a significantly less potent COMT inhibitor than tolcapone and has a much shorter in-vivo half-life. This means that entacapone has a very limited duration of effect and as a consequence, the drug must be administered in very high doses with every dose of L-DOPA taken by the patient. As such, the clinical efficacy of entacapone has been questioned—indeed a recent study (Parashos, S. A. et al., Clin. Neuropharmacol., 27(3): 119-123, 2004) revealed that the principal reason for discontinuation of entacapone treatment in Parkinson's disease patients was a perceived lack of efficacy.

Accordingly, there is still a need for COMT inhibitors exhibiting balanced properties of bioactivity, bioavailability and safety, with a long duration of action.

We have now surprisingly found that compounds of general formula I are COMT inhibitors which are endowed with such properties and exhibit an exceptionally long duration of action.

Compounds of the invention preferably have general formula I as defined below:

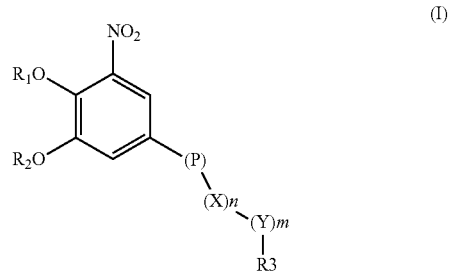

wherein $R_1$ and $R_2$ are independently from each other hydrogen or a group which is hydrolysable under physiological conditions, optionally substituted lower alkanoyl or aroyl; X represents a methylene group; Y represents an atom of oxygen, nitrogen or sulphur; n represents the number 0, 1, 2 or 3 and m represents the number 0 or 1; $R_3$ represents a pyridine group according to the formula A, B or C, which is connected as indicated by the unmarked bond:

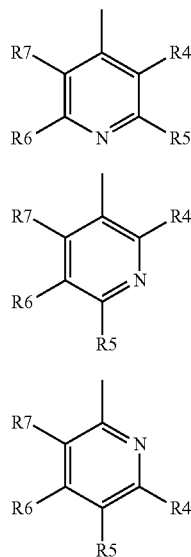

where $R_4$, $R_5$, $R_6$ and $R_7$ independently from each other represent hydrogen, $C_1$-$C_6$-alkyl, $C_1$-$C_6$-thioalkyl, $C_1$-$C_6$-alkoxy, $C_6$-$C_{12}$-aryloxy or a $C_6$-$C_{12}$-thioaryl group, $C_1$-$C_6$-alkanoyl or $C_7$-$C_{13}$-aroyl group, amino, $C_1$-$C_6$-alkylamino, $C_1$-$C_6$-dialkylamino, $C_3$-$C_{12}$-cycloalkylamino, $C_3$-$C_{12}$-heterocycloalkylamino, $C_1$-$C_6$-alkylsulphonyl, $C_6$-$C_{12}$-arylsulphonyl, halogen, $C_1$-$C_6$-haloalkyl, trifluoromethyl, cyano, nitro or a heteroaryl group; or two or more of residues $R_4$, $R_5$, $R_6$ and $R_7$ taken together represent aliphatic or heteroaliphatic rings or aromatic or heteroaromatic rings and wherein P represents a central unit, which is preferably a planar unit and which is even more preferably selected from the regioisomers of 1,3,4-oxadiazol-2,5-diyl, 1,2,4-oxadiazol-3,5-diyl, 4-methyl-4H-1,2,4-triazol-3,5-diyl, 1,3,5-triazin-2,4-diyl, 1,2,4-triazin-3,5-diyl, 2H-tetrazol-2,5-diyl, 1,2,3-thiadiazol-4,5-diyl, 1-alkyl-3-(alkoxycarbonyl)-1H-pyrrol-2,5-diyl, wherein alkyl is represented by methyl, ethyl, n-propyl and n-butyl and wherein alkoxy is represented by methoxy, ethoxy, n-propoxy and isopropoxy, 1-alkyl-1H-pyrrol-2,5-diyl, wherein alkyl is represented by methyl, ethyl, n-propyl and n-butyl, thiazol-2,4-diyl, 1-H-pyrazol-1,5-diyl, pyrimidin-2,4-diyl, oxazol-2,4-diyl, carbonyl, 1H-imidazol-1,5-diyl, isoxazol-3,5-diyl, furan-2,4-diyl, 3-alkoxycarbonylfuran-2,4-diyl, wherein alkoxy is represented by methoxy, ethoxy, n-propoxy and isopropoxy, benzene-1,3-diyl and (Z)-1-cyanoethen-1,2-diyl.

In the above definition, the regioisomers of the central unit include both regioisomers realizable by exchange of the nitrocatechol moiety and the —$(X)_n$—$(Y)_m$—$R_3$ moiety.

Preferably, $C_1$-$C_6$-alkyl residues represent methyl, ethyl, n-propyl, isopropyl, n-butyl, sec-butyl, tert-butyl, pentyl or hexyl. Preferably, $C_1$-$C_6$-thioalkyl residues represent thiomethyl, thioethyl, thio-n-propyl, thio-isopropyl, thio-n-butyl, thio-n-pentyl and thio-n-hexyl. Preferably, $C_1$-$C_6$-alkoxy residues represent methoxy, ethoxy, n-propoxy, isopropoxy, n-butoxy, sec-butoxy and tert-butoxy. Preferably, $C_6$-$C_{12}$-aryloxy residues represent phenoxy or naphthoxy which may optionally be substituted. Preferably, $C_6$-$C_{12}$-thioaryl residues represent thiophenyl and thionaphthyl which may optionally be substituted. Preferably, $C_1$-$C_6$-alkanoyl residues represent methanoyl, ethanoyl, propanoyl or butanoyl. Preferably, $C_7$-$C_{13}$-aroyl residues represent benzoyl and naphthoyl. Preferably, $C_1$-$C_6$-alkylamino residues represent methylamino, ethylamino, n-propylamino, isopropylamino and n-butylamino. Preferably, $C_1$-$C_6$-dialkylamino residues represent dimethylamino, diethylamino, di-n-propylamino, di-n-butylamino, di-isopropylamino, methylethylamino, methylpropylamino and ethylpropylamino. Preferably, $C_3$-$C_{12}$-cycloalkylamino residues represent pyrrolidino, piperidino, cyclo-hexylamino and dicyclohexylamino. Preferably, $C_3$-$C_{12}$-heterocloalkylamino residues represent morpholino, 2,6-dimethylmorpholino, 3,5-dimethylmorpholino, piperazino, N-methylpiperazino and N-ethylpiperazino. Preferably, $C_1$-$C_6$-alkylsulphonyl or $C_6$-$C_{12}$-arylsulphonyl residues represent methylsulfonyl, ethylsulfonyl, phenylsulfonyl, and tolylsulfonyl. Preferably, halogen residues represent chloro, bromo, iodo and fluoro. Preferably, $C_1$-$C_6$-haloalkyl represents chloromethyl, fluoromethyl, dichloromethyl, difluoromethyl, tri-chloromethyl and trifluoromethyl. Preferably, heteroaryl residues represent pyridyl, pyrimidyl, isoxazolyl, oxazolyl, isoxadiazolyl, oxadiazolyl, triazolyl and tetrazolyl. In cases where two or more of residues $R_4$, $R_5$, $R_6$ and $R_7$ taken together represent aliphatic or heteroaliphatic rings or aromatic or heteroaromatic rings, preferred combined residues are indolizinyl, isoindolyl, indolyl, indazolyl, purinyl, quinolizinyl, naphthyridinyl, isoquinolyl and quinolyl.

We have surprisingly found that compounds of general formula I markedly enhance the bioavailability of L-DOPA, increase the delivery of L-DOPA to the brain and significantly augment the levels of dopamine in the brain over extended periods. Compounds of general formula I not only inhibit COMT, thus preventing breakdown of L-DOPA, but also have the additional effect of increasing L-DOPA bioavailability. These effects upon L-DOPA levels after the administration of compounds of general formula I are markedly greater than those observed with tolcapone, the only COMT inhibitor thusfar known to be endowed with a reasonably long duration of action.

Moreover, even after long onset times (e.g. 24 h after administration), compounds of general formula I produce increases in L-DOPA delivery to the brain similar to those observed at shorter time points (e.g. 2 and 7 h), which contrasts to that observed with tolcapone. This results in a more steady delivery of L-DOPA to the brain after the administration of compounds of general formula I, whereas tolcapone is prone to produce marked oscillations in the brain delivery of L-DOPA, which provokes undesirable side-effects in Parkinsonian patients.

Thus compounds of general formula I may therefore be endowed with therapeutic advantages due to sustained and constant elevation of L-DOPA levels whilst the use of tolcapone induces dyskinesias in patients due to abrupt oscillations in L-DOPA levels.

The bioavailability, bioactivity, safety profile and other related properties known in the art (e.g. blood-brain-barrier permeability) can be routinely optimized by the skilled person on basis of the teaching of the present application by varying substituents $R_1$-$R_7$ of general formula I in order to obtain a desirable balanced mix of properties.

Preferred compounds of the above general formula (I) having a 4-methyl-4H-1,2,4-triazol-3,5-diyl as central unit include 5-(4-methyl-5-(4-(trifluoromethyl)pyridin-3-yl)-4H-1,2,4-triazol-3-yl)-3-nitrobenzene-1,2-diol, 5-(5-(2- chloro-4,6-dimethylpyridin-3-yl)-4-methyl-4H-1,2,4-triazol-3-yl)-3-nitrobenzene-1,2-diol, 5-(4-methyl-5-(2-methyl-6-(trifluoromethyl)pyridin-3-yl)-4H-1,2,4-triazol-3-yl)-3-nitrobenzene-1,2-diol, 5-(4-methyl-5-(6-(trifluoromethyl)pyridin-3-yl)-4H-1,2,4-triazol-3-yl)-3-nitrobenzene-1,2-diol, 5-(4-methyl-5-(6-methyl-4-(trifluoromethyl)pyridin-3-yl)-4H-1,2,4-triazol-3-yl)-3-nitrobenzene-1,2-diol, 5-(5-(2,6-dimethyl-4-(trifluoromethyl)pyridin-3-yl)-4-methyl-4H-1,2,4-triazol-3-yl)-3-nitrobenzene-1,2-diol, 5-(5-(3,5-dichloropyridin-4-yl)-4-methyl-4H-1,2,4-triazol-3-yl)-3-nitrobenzene-1,2-diol, 5-(4-methyl-5-(6-methyl-2-phenyl-4-(trifluoromethyl)pyridin-3-yl)-4H-1,2,4-triazol-3-yl)-3-nitrobenzene-1,2-diol, 5-(5-(2-bromo-4,5,6-trimethylpyridin-3-yl)-4-methyl-4H-1,2,4-triazol-3-yl)-3-nitrobenzene-1,2-diol, 5-(5-(2-chloro-4,5,6-trimethylpyridin-3-yl)-4-methyl-4H-1,2,4-triazol-3-yl)-3-nitrobenzene-1,2-diol, 5-(4-methyl-5-(2-(trifluoromethyl)pyridin-3-yl)-4H-1,2,4-triazol-3-yl)-3-nitrobenzene-1,2-diol, 5-(5-(2,5-dichloro-4,6-dimethylpyridin-3-yl)-4-methyl-4H-1,2,4-triazol-3-yl)-3-nitrobenzene-1,2-diol, 5-(4-methyl-5-(5-(trifluoromethyl)pyridin-3-yl)-4H-1,2,4-triazol-3-yl)-3-nitrobenzene-1,2-diol, 5-(5-(2-fluoropyridin-3-yl)-4-methyl-4H-1,2,4-triazol-3-yl)-3-nitrobenzene-1,2-diol, 5-(5-(2-fluoropyridin-4-yl)-4-methyl-4H-1,2,4-triazol-3-yl)-3-nitrobenzene-1,2-diol, 5-(5-(6-fluoropyridin-2-yl)-4-methyl-4H-1,2,4-triazol-3-yl)-3-nitrobenzene-1,2-diol, 5-(5-(2-chloro-6-methylpyridin-3-yl)-4-methyl-4H-1,2,4-triazol-3-yl)-3-nitrobenzene-1,2-diol, 5-(5-(2-bromo-6-methylpyridin-3-yl)-4-methyl-4H-1,2,4-triazol-3-yl)-3-nitrobenzene-1,2-diol, 5-(5-(2-bromo-5-chloro-4,6-dimethylpyridin-3-yl)-4-methyl-4H-1,2,4-triazol-3-yl)-3-nitrobenzene-1,2-diol.

Preferred compounds of the above general formula (I) having a 1,3,5-triazin-2,4-diyl as central unit include 3-nitro-5-(4-(4-(trifluoromethyl)pyridin-3-yl)-1,3,5-triazin-2-yl)benzene-1,2-diol, 5-(4-(2-methyl-6-(trifluoromethyl)pyridin-3-yl)-1,3,5-triazin-2-yl)-3-nitrobenzene-1,2-diol, 3-nitro-5-(4-(6-(trifluoromethyl)pyridin-3-yl)-1,3,5-triazin-2-yl)benzene-1,2-diol, 5-(4-(6-methyl-4-(trifluoromethyl)pyridin-3-yl)-1,3,5-triazin-2-yl)-3-nitrobenzene-1,2-diol, 5-(4-(2,6-dimethyl-4-(trifluoromethyl)pyridin-3-yl)-1,3,5-triazin-2-yl)-3-nitrobenzene-1,2-diol, 5-(4-(6-methyl-2-phenyl-4-(trifluoromethyl)pyridin-3-yl)-1,3,5-triazin-2-yl)-3-nitrobenzene-1,2-diol, 3-nitro-5-(4-(2-(trifluoromethyl)pyridin-3-yl)-1,3,5-triazin-2-yl)benzene-1,2-diol, 3-nitro-5-(4-(5-(trifluoromethyl)pyridin-3-yl)-1,3,5-triazin-2-yl)benzene-1,2-diol.

Preferred compounds of the above general formula (I) having a 1,2,4-triazin-3,5-diyl as a central unit include 3-nitro-5-(3-(4-(trifluoromethyl)pyridin-3-yl)-1,2,4-triazin-5-yl)benzene-1,2-diol, 5-(3-(2-methyl-6-(trifluoromethyl)pyridin-3-yl)-1,2,4-triazin-5-yl)-3-nitrobenzene-1,2-diol, 3-nitro-5-(3-(6-(trifluoromethyl)pyridin-3-yl)-1,2,4-triazin-5-yl)benzene-1,2-diol, 5-(3-(6-methyl-4-(trifluoromethyl)pyridin-3-yl)-1,2,4-triazin-5-yl)-3-nitrobenzene-1,2-diol, 5-(3-(2,6-dimethyl-4-(trifluoromethyl)pyridin-3-yl)-1,2,4-triazin-5-yl)-3-nitrobenzene-1,2-diol, 5-(3-(6-methyl-2-phenyl-4-(trifluoromethyl)pyridin-3-yl)-1,2,4-triazin-5-yl)-3-nitrobenzene-1,2-diol, 3-nitro-5-(3-(2-(trifluoromethyl)pyridin-3-yl)-1,2,4-triazin-5-yl)benzene-1,2-diol, 3-nitro-5-(3-(5-(trifluoromethyl)pyridin-3-yl)-1,2,4-triazin-5-yl)benzene-1,2-diol, 5-(3-(2-fluoropyridin-4-yl)-1,2,4-triazin-5-yl)-3-nitrobenzene-1,2-diol, 5-(3-(6-fluoropyridin-2-yl)-1,2,4-triazin-5-yl)-3-nitrobenzene-1,2-diol.

Preferred compounds of the above general formula (I) having a 1,2,4-oxadiazol-3,5-diyl as central unit include 3-nitro-5-(3-(4-(trifluoromethyl)pyridin-3-yl)-1,2,4-oxadiazol-5-yl)benzene-1,2-diol, 5-(3-(2-chloro-4,6-dimethylpyridin-3-yl)-1,2,4-oxadiazol-5-yl)-3-nitrobenzene-1,2-diol, 5-(3-(2-methyl-6-(trifluoromethyl)pyridin-3-yl)-1,2,4-oxadiazol-5-yl)-3-nitrobenzene-1,2-diol, 3-nitro-5-(3-(6-(trifluoromethyl)pyridin-3-yl)-1,2,4-oxadiazol-5-yl)benzene-1,2-diol, 5-(3-(6-methyl-4-(trifluoromethyl)pyridin-3-yl)-1,2,4-oxadiazol-5-yl)-3-nitrobenzene-1,2-diol, 5-(3-(2,6-dimethyl-4-(trifluoromethyl)pyridin-3-yl)-1,2,4-oxadiazol-5-yl)-3-nitrobenzene-1,2-diol, 5-(3-(3,5-dichloropyridin-4-yl)-1,2,4-oxadiazol-5-yl)-3-nitrobenzene-1,2-diol, 5-(3-(6-methyl-2-phenyl-4-(trifluoromethyl)pyridin-3-yl)-1,2,4-oxadiazol-5-yl)-3-nitrobenzene-1,2-diol, 5-(3-(2-bromo-4,5,6-trimethylpyridin-3-yl)-1,2,4-oxadiazol-5-yl)-3-nitrobenzene-1,2-diol, 5-(3-(2-chloro-4,5,6-trimethylpyridin-3-yl)-1,2,4-oxadiazol-5-yl)-3-nitrobenzene-1,2-diol, 3-nitro-5-(3-(2-(trifluoromethyl)pyridin-3-yl)-1,2,4-oxadiazol-5-yl)benzene-1,2-diol, 5-(3-(2,5-dichloro-4,6-dimethylpyridin-3-yl)-1,2,4-oxadiazol-5-yl)-3-nitrobenzene-1,2-diol, 3-nitro-5-(3-(5-(trifluoromethyl)pyridin-3-yl)-1,2,4-oxadiazol-5-yl)benzene-1,2-diol, 5-(3-(2-fluoropyridin-3-yl)-1,2,4-oxadiazol-5-yl)-3-nitrobenzene-1,2-diol, 5-(3-(2-fluoropyridin-4-yl)-1,2,4-oxadiazol-5-yl)-3-nitrobenzene-1,2-diol, 5-(3-(6-fluoropyridin-2-yl)-1,2,4-oxadiazol-5-yl)-3-nitrobenzene-1,2-diol, 5-(3-(2-chloro-6-methylpyridin-3-yl)-1,2,4-oxadiazol-5-yl)-3-nitrobenzene-1,2-diol, 5-(3-(2-bromo-6-methylpyridin-3-yl)-1,2,4-oxadiazol-5-yl)-3-nitrobenzene-1,2-diol, 5-(3-(2-bromo-5-chloro-4,6-dimethylpyridin-3-yl)-1,2,4-oxadiazol-5-yl)-3-nitrobenzene-1,2-diol, 3-nitro-5-(5-(4-(trifluoromethyl)pyridin-3-yl)-1,2,4-oxadiazol-3-yl)benzene-1,2-diol, 5-(5-(2-chloro-4,6-dimethylpyridin-3-yl)-1,2,4-oxadiazol-3-yl)-3-nitrobenzene-1,2-diol, 5-(5-(2-methyl-6-(trifluoromethyl)pyridin-3-yl)-1,2,4-oxadiazol-3-yl)-3-nitrobenzene-1,2-diol, 3-nitro-5-(5-(6-(trifluoromethyl)pyridin-3-yl)-1,2,4-oxadiazol-3-yl)benzene-1,2-diol, 5-(5-(6-methyl-4-(trifluoromethyl)pyridin-3-yl)-1,2,4-oxadiazol-3-yl)-3-nitrobenzene-1,2-diol, 5-(5-(2,6-dimethyl-4-(trifluoromethyl)pyridin-3-yl)-1,2,4-oxadiazol-3-yl)-3-nitrobenzene-1,2-diol, 5-(5-(3,5-dichloropyridin-4-yl)-1,2,4-oxadiazol-3-yl)-3-nitrobenzene-1,2-diol, 5-(5-(6-methyl-2-phenyl-4-(trifluoromethyl)pyridin-3-yl)-1,2,4-oxadiazol-3-yl)-3-nitrobenzene-1,2-diol, 5-(5-(2-bromo-4,5,6-trimethylpyridin-3-yl)-1,2,4-oxadiazol-3-yl)-3-nitrobenzene-1,2-diol, 5-(5-(2-chloro-4,5,6-trimethylpyridin-3-yl)-1,2,4-oxadiazol-3-yl)-3-nitrobenzene-1,2-diol, 3-nitro-5-(5-(2-(trifluoromethyl)pyridin-3-yl)-1,2,4-oxadiazol-3-yl)benzene-1,2-diol, 5-(5-(2,5-dichloro-4,6-dimethylpyridin-3-yl)-1,2,4-oxadiazol-3-yl)-3-nitrobenzene-1,2-diol, 3-nitro-5-(5-(5-(trifluoromethyl)pyridin-3-yl)-1,2,4-oxadiazol-3-yl)benzene-1,2-diol, 5-(5-(2-fluoropyridin-3-yl)-1,2,4-oxadiazol-3-yl)-3-nitrobenzene-1,2-diol, 5-(5-(2-fluoropyridin-4-yl)-1,2,4-oxadiazol-3-yl)-3-nitrobenzene-1,2-diol, 5-(5-(6-fluoropyridin-2-yl)-1,2,4-oxadiazol-3-yl)-3-nitrobenzene-1,2-diol, 5-(5-(2-chloro-6-methylpyridin-3-yl)-1,2,4-oxadiazol-3-yl)-3-nitrobenzene-1,2-diol, 5-(5-(2-bromo-6-methylpyridin-3-yl)-1,2,4-oxadiazol-3-yl)-3-nitrobenzene-1,2-diol, 5-(5-(2-bromo-5-chloro-4,6-dimethylpyridin-3-yl)-1,2,4-oxadiazol-3-yl)-3-nitrobenzene-1,2-diol.

Preferred compounds of the above general formula (I) having a 1,3,4-oxadiazol-2,5-diyl as central unit include 3-nitro-5-(5-(4-(trifluoromethyl)pyridin-3-yl)-1,3,4-oxadiazol-2-yl)benzene-1,2-diol, 5-(5-(2-chloro-4,6-dimethylpyridin-3-yl)-1,3,4-oxadiazol-2-yl)-3-nitrobenzene-1,2-diol, 5-(5-(2-methyl-6-(trifluoromethyl)pyridin-3-yl)-1,3,4- oxadiazol-2-yl)-3-nitrobenzene-1,2-diol, 3-nitro-5-(5-(6-(trifluoromethyl)pyridin-3-yl)-1,3,4-oxadiazol-2-yl)benzene-1,2-diol, 5-(5-(6-methyl-4-(trifluoromethyl)pyridin-3-yl)-1,3,4-oxadiazol-2-yl)-3-nitrobenzene-1,2-diol, 5-(5-(2,6-dimethyl-4-(trifluoromethyl)pyridin-3-yl)-1,3,4-oxadiazol-2-yl)-3-nitrobenzene-1,2-diol, 5-(5-(3,5-dichloropyridin-4-yl)-1,3,4-oxadiazol-2-yl)-3-nitrobenzene-1,2-diol, 5-(5-(6-methyl-2-phenyl-4-(trifluoromethyl)pyridin-3-yl)-1,3,4-oxadiazol-2-yl)-3-nitrobenzene-1,2-diol, 5-(5-(2-bromo-4,5,6-trimethylpyridin-3-yl)-1,3,4-oxadiazol-2-yl)-3-nitrobenzene-1,2-diol, 5-(5-(2-chloro-4,5,6-trimethylpyridin-3-yl)-1,3,4-oxadiazol-2-yl)-3-nitrobenzene-1,2-diol, 3-nitro-5-(5-(2-(trifluoromethyl)pyridin-3-yl)-1,3,4-oxadiazol-2-yl)benzene-1,2-diol, 5-(5-(2,5-dichloro-4,6-dimethylpyridin-3-yl)-1,3,4-oxadiazol-2-yl)-3-nitrobenzene-1,2-diol, 3-nitro-5-(5-(5-(trifluoromethyl)pyridin-3-yl)-1,3,4-oxadiazol-2-yl)benzene-1,2-diol, 5-(5-(2-fluoropyridin-3-yl)-1,3,4-oxadiazol-2-yl)-3-nitrobenzene-1,2-diol, 5-(5-(2-fluoropyridin-4-yl)-1,3,4-oxadiazol-2-yl)-3-nitrobenzene-1,2-diol, 5-(5-(6-fluoropyridin-2-yl)-1,3,4-oxadiazol-2-yl)-3-nitrobenzene-1,2-diol, 5-(5-(2-chloro-6-methylpyridin-3-yl)-1,3,4-oxadiazol-2-yl)-3-nitrobenzene-1,2-diol, 5-(5-(2-bromo-6-methylpyridin-3-yl)-1,3,4-oxadiazol-2-yl)-3-nitrobenzene-1,2-diol, 5-(5-(2-bromo-5-chloro-4,6-dimethylpyridin-3-yl)-1,3,4-oxadiazol-2-yl)-3-nitrobenzene-1,2-diol.

Preferred compounds of the above general formula (I) having a (Z)-1-cyanoethen-1,2-diyl moiety as central unit include (Z)-3-(3,4-dihydroxy-5-nitrophenyl)-2-(4-(trifluoromethyl)pyridin-3-yl)acrylonitrile, (Z)-2-(2-chloro-4,6-dimethylpyridin-3-yl)-3-(3,4-dihydroxy-5-nitrophenyl)acrylonitrile, (Z)-3-(3,4-dihydroxy-5-nitrophenyl)-2-(2-methyl-6-(trifluoromethyl)pyridin-3-yl)acrylonitrile, (Z)-3-(3,4-dihydroxy-5-nitrophenyl)-2-(6-(trifluoromethyl)pyridin-3-yl)acrylonitrile, (Z)-3-(3,4-dihydroxy-5-nitrophenyl)-2-(6-methyl-4-(trifluoromethyl)pyridin-3-yl)acrylonitrile, (Z)-3-(3,4-dihydroxy-5-nitrophenyl)-2-(2,6-dimethyl-4-(trifluoromethyl)pyridin-3-yl)acrylonitrile, (Z)-2-(3,5-dichloropyridin-4-yl)-3-(3,4-dihydroxy-5-nitrophenyl)acrylonitrile, (Z)-3-(3,4-dihydroxy-5-nitrophenyl)-2-(6-methyl-2-phenyl-4-(trifluoromethyl)pyridin-3-yl)acrylonitrile, (Z)-2-(2-bromo-4,5,6-trimethylpyridin-3-yl)-3-(3,4-dihydroxy-5-nitrophenyl)acrylonitrile, (Z)-2-(2-chloro-4,5,6-trimethylpyridin-3-yl)-3-(3,4-dihydroxy-5-nitrophenyl)acrylonitrile, (Z)-3-(3,4-dihydroxy-5-nitrophenyl)-2-(2-(trifluoromethyl)pyridin-3-yl)acrylonitrile, (Z)-2-(2,5-dichloro-4,6-dimethylpyridin-3-yl)-3-(3,4-dihydroxy-5-nitrophenyl)acrylonitrile, (Z)-3-(3,4-dihydroxy-5-nitrophenyl)-2-(5-(trifluoromethyl)pyridin-3-yl)acrylonitrile, (Z)-3-(3,4-dihydroxy-5-nitrophenyl)-2-(2-fluoropyridin-3-yl)acrylonitrile, (Z)-3-(3,4-dihydroxy-5-nitrophenyl)-2-(2-fluoropyridin-4-yl)acrylonitrile, (Z)-3-(3,4-dihydroxy-5-nitrophenyl)-2-(6-fluoropyridin-2-yl)acrylonitrile, (Z)-2-(2-chloro-6-methylpyridin-3-yl)-3-(3,4-dihydroxy-5-nitrophenyl)acrylonitrile, (Z)-2-(2-bromo-6-methylpyridin-3-yl)-3-(3,4-dihydroxy-5-nitrophenyl)acrylonitrile, (Z)-2-(2-bromo-5-chloro-4,6-dimethylpyridin-3-yl)-3-(3,4-dihydroxy-5-nitrophenyl)acrylonitrile.

Preferred compounds of the above general formula (I) having as central unit a furan-2,4-diyl or a 3-alkoxycarbonylfuran-2,4-diyl moiety, wherein alkoxy is represented by methoxy, ethoxy, n-propoxy and isopropoxy, include ethyl 4-(3,4-dihydroxy-5-nitrophenyl)-2-(4-(trifluoromethyl)pyridin-3-yl)furan-3-carboxylate, ethyl 2-(2-chloro-4,6-dimethylpyridin-3-yl)-4-(3,4-dihydroxy-5-nitrophenyl)furan-3-carboxylate, ethyl 4-(3,4-dihydroxy-5-nitrophenyl)-2-(2-methyl-6-(trifluoromethyl)pyridin-3-yl)furan-3-carboxylate, ethyl 4-(3,4-dihydroxy-5-nitrophenyl)-2-(6-(trifluoromethyl)pyridin-3-yl)furan-3-carboxylate, ethyl 4-(3,4-dihydroxy-5-nitrophenyl)-2-(6-methyl-4-(trifluoromethyl)pyridin-3-yl)furan-3-carboxylate, ethyl 4-(3,4-dihydroxy-5-nitrophenyl)-2-(2,6-dimethyl-4-(trifluoromethyl)pyridin-3-yl)furan-3-carboxylate, ethyl 2-(3,5-dichloropyridin-4-yl)-4-(3,4-dihydroxy-5-nitrophenyl)furan-3-carboxylate, 5-(5-(6-methyl-2-phenyl-4-(trifluoromethyl)pyridin-3-yl)furan-3-yl)-3-nitrobenzene-1,2-diol, 5-(5-(2-bromo-4,5,6-trimethylpyridin-3-yl)furan-3-yl)-3-nitrobenzene-1,2-diol, 5-(5-(2-chloro-4,5,6-trimethylpyridin-3-yl)furan-3-yl)-3-nitrobenzene-1,2-diol, 3-nitro-5-(5-(2-(trifluoromethyl)pyridin-3-yl)furan-3-yl)benzene-1,2-diol, 5-(5-(2,5-dichloro-4,6-dimethylpyridin-3-yl)furan-3-yl)-3-nitrobenzene-1,2-diol, 3-nitro-5-(5-(5-(trifluoromethyl)pyridin-3-yl)furan-3-yl)benzene-1,2-diol, ethyl 4-(3,4-dihydroxy-5-nitrophenyl)-2-(2-fluoropyridin-3-yl)furan-3-carboxylate, ethyl 4-(3,4-dihydroxy-5-nitrophenyl)-2-(2-fluoropyridin-4-yl)furan-3-carboxylate, ethyl 4-(3,4-dihydroxy-5-nitrophenyl)-2-(6-fluoropyridin-2-yl)furan-3-carboxylate, ethyl 2-(2-chloro-6-methylpyridin-3-yl)-4-(3,4-dihydroxy-5-nitrophenyl)furan-3-carboxylate, ethyl 2-(2-bromo-6-methylpyridin-3-yl)-4-(3,4-dihydroxy-5-nitrophenyl)furan-3-carboxylate, ethyl 2-(2-bromo-5-chloro-4,6-dimethylpyridin-3-yl)-4-(3,4-dihydroxy-5-nitrophenyl)furan-3-carboxylate.

Preferred compounds of the above general formula (I) having as central unit a 1H-imidazol-1,5-diyl moiety include 3-nitro-5-(1-(4-(trifluoromethyl)pyridin-3-yl)-1H-imidazol-5-yl)benzene-1,2-diol, 5-(1-(2-chloro-4,6-dimethylpyridin-3-yl)-1H-imidazol-5-yl)-3-nitrobenzene-1,2-diol, 5-(1-(2-methyl-6-(trifluoromethyl)pyridin-3-yl)-1H-imidazol-5-yl)-3-nitrobenzene-1,2-diol, 3-nitro-5-(1-(6-(trifluoromethyl)pyridin-3-yl)-1H-imidazol-5-yl)benzene-1,2-diol, 5-(1-(3,5-dichloropyridin-4-yl)-1H-imidazol-5-yl)-3-nitrobenzene-1,2-diol, 3-nitro-5-(1-(2-(trifluoromethyl)pyridin-3-yl)-1H-imidazol-5-yl)benzene-1,2-diol, 3-nitro-5-(1-(5-(trifluoromethyl)pyridin-3-yl)-1H-imidazol-5-yl)benzene-1,2-diol, 5-(1-(2-fluoropyridin-3-yl)-1H-imidazol-5-yl)-3-nitrobenzene-1,2-diol, 5-(1-(6-fluoropyridin-2-yl)-1H-imidazol-5-yl)-3-nitrobenzene-1,2-diol, 5-(1-(2-chloro-6-methylpyridin-3-yl)-1H-imidazol-5-yl)-3-nitrobenzene-1,2-diol, 5-(1-(2-bromo-6-methylpyridin-3-yl)-1H-imidazol-5-yl)-3-nitrobenzene-1,2-diol.

Preferred compounds of the above general formula (I) having as central unit a isoxazol-3,5-diyl moiety include 3-nitro-5-(5-(4-(trifluoromethyl)pyridin-3-yl)isoxazol-3-yl)benzene-1,2-diol, 5-(5-(2-chloro-4,6-dimethylpyridin-3-yl)isoxazol-3-yl)-3-nitrobenzene-1,2-diol, 5-(5-(2-methyl-6-(trifluoromethyl)pyridin-3-yl)isoxazol-3-yl)-3-nitrobenzene-1,2-diol, 3-nitro-5-(5-(6-(trifluoromethyl)pyridin-3-yl)isoxazol-3-yl)benzene-1,2-diol, 5-(5-(6-methyl-4-(trifluoro-methyl)pyridin-3-yl)isoxazol-3-yl)-3-nitrobenzene-1,2-diol, 5-(5-(2,6-dimethyl-4-(trifluoromethyl)pyridin-3-yl)isoxazol-3-yl)-3-nitrobenzene-1,2-diol, 5-(5-(3,5-dichloropyridin-4-yl)isoxazol-3-yl)-3-nitrobenzene-1,2-diol, 5-(5-(6-methyl-2-phenyl-4-(trifluoromethyl)pyridin-3-yl)isoxazol-3-yl)-3-nitrobenzene-1,2-diol, 5-(5-(2-bromo-4,5,6-trimethylpyridin-3-yl)isoxazol-3-yl)-3-nitrobenzene-1,2-diol, 5-(5-(2-chloro-4,5,6-trimethylpyridin-3-yl)isoxazol-3-yl)-3-nitrobenzene-1,2-diol, 3-nitro-5-(5-(2-(trifluoromethyl)pyridin-3-yl)isoxazol-3-yl)benzene-1,2-diol, 5-(5-(2,5-dichloro-4,6-dimethylpyridin-3-yl)isoxazol-3-yl)-3-nitrobenzene-1,2-diol, 3-nitro-5-(5-(5-(trifluoromethyl)pyridin-3-yl)isoxazol-3-yl)benzene-1,2- diol, 5-(5-(2-fluoropyridin-3-yl)isoxazol-3-yl)-3-nitrobenzene-1,2-diol, 5-(5-(2-fluoropyridin-4-yl)isoxazol-3-yl)-3-nitrobenzene-1,2-diol, 5-(5-(6-fluoropyridin-2-yl)isoxazol-3-yl)-3-nitrobenzene-1,2-diol, 5-(5-(2-chloro-6-methylpyridin-3-yl)isoxazol-3-yl)-3-nitrobenzene-1,2-diol, 5-(5-(2-bromo-6-methylpyridin-3-yl)isoxazol-3-yl)-3-nitrobenzene-1,2-diol, 5-(5-(2-bromo-5-chloro-4,6-dimethylpyridin-3-yl)isoxazol-3-yl)-3-nitrobenzene-1,2-diol.

Preferred compounds of the above general formula (I) having as central unit a carbonyl moiety include (3,4-dihydroxy-5-nitrophenyl)(4-(trifluoromethyl)pyridin-3-yl)methanone, (2-chloro-4,6-dimethylpyridin-3-yl)(3,4-dihydroxy-5-nitrophenyl)methanone, (3,4-dihydroxy-5-nitrophenyl)(2-methyl-6-(trifluoromethyl)pyridin-3-yl)methanone, (3,4-dihydroxy-5-nitrophenyl)(6-(trifluoromethyl)pyridin-3-yl)methanone, (3,4-dihydroxy-5-nitrophenyl)(6-methyl-4-(trifluoromethyl)pyridin-3-yl)methanone, (3,4-dihydroxy-5-nitrophenyl)(2,6-dimethyl-4-(trifluoromethyl)pyridin-3-yl)methanone, (3,5-dichloropyridin-4-yl)(3,4-dihydroxy-5-nitrophenyl)methanone, (3,4-dihydroxy-5-nitrophenyl)(6-methyl-2-phenyl-4-(trifluoromethyl)pyridin-3-yl)methanone, (2-bromo-4,5,6-trimethylpyridin-3-yl)(3,4-dihydroxy-5-nitrophenyl)methanone, (2-chloro-4,5,6-trimethylpyridin-3-yl)(3,4-dihydroxy-5-nitrophenyl)methanone, (3,4-dihydroxy-5-nitrophenyl)(2-(trifluoromethyl)pyridin-3-yl)methanone, (2,5-dichloro-4,6-dimethylpyridin-3-yl)(3,4-dihydroxy-5-nitrophenyl)methanone, (3,4-dihydroxy-5-nitrophenyl)(5-(trifluoromethyl)pyridin-3-yl)methanone, (3,4-dihydroxy-5-nitrophenyl)(2-fluoropyridin-3-yl)methanone, (3,4-dihydroxy-5-nitrophenyl)(2-fluoropyridin-4-yl)methanone, (3,4-dihydroxy-5-nitrophenyl)(6-fluoropyridin-2-yl)methanone, (2-chloro-6-methylpyridin-3-yl)(3,4-dihydroxy-5-nitrophenyl)methanone, (2-bromo-6-methylpyridin-3-yl)(3,4-dihydroxy-5-nitrophenyl)methanone, (2-bromo-5-chloro-4,6-dimethylpyridin-3-yl)(3,4-dihydroxy-5-nitrophenyl)methanone.

Preferred compounds of the above general formula (I) having as central unit an oxazol-2,4-diyl moiety include 3-nitro-5-(2-(4-(trifluoromethyl)pyridin-3-yl)oxazol-4-yl)benzene-1,2-diol, 5-(2-(2-chloro-4,6-dimethylpyridin-3-yl)oxazol-4-yl)-3-nitrobenzene-1,2-diol, 5-(2-(2-methyl-6-(trifluoromethyl)pyridin-3-yl)oxazol-4-yl)-3-nitrobenzene-1,2-diol, 3-nitro-5-(2-(6-(trifluoromethyl)pyridin-3-yl)oxazol-4-yl)benzene-1,2-diol, 5-(2-(6-methyl-4-(trifluoromethyl)pyridin-3-yl)oxazol-4-yl)-3-nitrobenzene-1,2-diol, 5-(2-(2,6-dimethyl-4-(trifluoromethyl)pyridin-3-yl)oxazol-4-yl)-3-nitrobenzene-1,2-diol, 5-(2-(3,5-dichloropyridin-4-yl)oxazol-4-yl)-3-nitrobenzene-1,2-diol, 5-(2-(6-methyl-2-phenyl-4-(trifluoromethyl)pyridin-3-yl)oxazol-4-yl)-3-nitrobenzene-1,2-diol, 5-(2-(2-bromo-4,5,6-trimethylpyridin-3-yl)oxazol-4-yl)-3-nitrobenzene-1,2-diol, 5-(2-(2-chloro-4,5,6-trimethylpyridin-3-yl)oxazol-4-yl)-3-nitrobenzene-1,2-diol, 3-nitro-5-(2-(2-(trifluoromethyl)pyridin-3-yl)oxazol-4-yl)benzene-1,2-diol, 5-(2-(2,5-dichloro-4,6-dimethylpyridin-3-yl)oxazol-4-yl)-3-nitrobenzene-1,2-diol, 3-nitro-5-(2-(5-(trifluoromethyl)pyridin-3-yl)oxazol-4-yl)benzene-1,2-diol, 5-(2-(2-fluoropyridin-3-yl)oxazol-4-yl)-3-nitrobenzene-1,2-diol, 5-(2-(2-fluoropyridin-4-yl)oxazol-4-yl)-3-nitrobenzene-1,2-diol, 5-(2-(6-fluoropyridin-2-yl)oxazol-4-yl)-3-nitrobenzene-1,2-diol, 5-(2-(2-chloro-6-methylpyridin-3-yl)oxazol-4-yl)-3-nitrobenzene-1,2-diol, 5-(2-(2-bromo-6-methylpyridin-3-yl)oxazol-4-yl)-3-nitrobenzene-1,2-diol, 5-(2-(2-bromo-5-chloro-4,6-dimethylpyridin-3-yl)oxazol-4-yl)-3-nitrobenzene-1,2-diol.

Preferred compounds of the above general formula (I) having as central unit an benzene-1,3-diyl moiety include 5-nitro-3'-(4-(trifluoromethyl)pyridin-3-yl)biphenyl-3,4-diol, 5-nitro-3'-(6-(trifluoromethyl)pyridin-3-yl)biphenyl-3,4-diol, 3'-(3,5-dichloropyridin-4-yl)-5-nitrobiphenyl-3,4-diol, 5-nitro-3'-(2-(trifluoromethyl)pyridin-3-yl)biphenyl-3,4-diol, 5-nitro-3'-(5-(trifluoromethyl)pyridin-3-yl)biphenyl-3,4-diol.

Preferred compounds of the above general formula (I) having as central unit an 1-H-pyrazol-1,5-diyl moiety include 3-nitro-5-(1-(4-(trifluoromethyl)pyridin-3-yl)-1H-pyrazol-5-yl)benzene-1,2-diol, 3-nitro-5-(1-(6-(trifluoromethyl)pyridin-3-yl)-1H-pyrazol-5-yl)benzene-1,2-diol, 5-(1-(3,5-dichloropyridin-4-yl)-1H-pyrazol-5-yl)-3-nitrobenzene-1,2-diol, 3-nitro-5-(1-(2-(trifluoromethyl)pyridin-3-yl)-1H-pyrazol-5-yl)benzene-1,2-diol, 3-nitro-5-(1-(5-(trifluoromethyl)pyridin-3-yl)-1H-pyrazol-5-yl)benzene-1,2-diol, 5-(1-(2-fluoropyridin-4-yl)-1H-pyrazol-5-yl)-3-nitrobenzene-1,2-diol.

Preferred compounds of the above general formula (I) having as central unit an pyrimidin-2,4-diyl moiety include 3-nitro-5-(2-(4-(trifluoromethyl)pyridin-3-yl)pyrimidin-4-yl)benzene-1,2-diol, 5-(2-(2-chloro-4,6-dimethylpyridin-3-yl)pyrimidin-4-yl)-3-nitrobenzene-1,2-diol, 5-(2-(2-methyl-6-(trifluoromethyl)pyridin-3-yl)pyrimidin-4-yl)-3-nitrobenzene-1,2-diol, 3-nitro-5-(2-(6-(trifluoromethyl)pyridin-3-yl)pyrimidin-4-yl)benzene-1,2-diol, 5-(2-(6-methyl-4-(trifluoromethyl)pyridin-3-yl)pyrimidin-4-yl)-3-nitrobenzene-1,2-diol, 5-(2-(2,6-dimethyl-4-(trifluoromethyl)pyridin-3-yl)pyrimidin-4-yl)-3-nitrobenzene-1,2-diol, 5-(2-(3,5-dichloropyridin-4-yl)pyrimidin-4-yl)-3-nitrobenzene-1,2-diol, 5-(2-(6-methyl-2-phenyl-4-(trifluoromethyl)pyridin-3-yl)pyrimidin-4-yl)-3-nitrobenzene-1,2-diol, 5-(2-(2-bromo-4,5,6-trimethylpyridin-3-yl)pyrimidin-4-yl)-3-nitrobenzene-1,2-diol, 5-(2-(2-chloro-4,5,6-trimethylpyridin-3-yl)pyrimidin-4-yl)-3-nitrobenzene-1,2-diol, 3-nitro-5-(2-(2-(trifluoromethyl)pyridin-3-yl)pyrimidin-4-yl)benzene-1,2-diol, 5-(2-(2,5-dichloro-4,6-dimethylpyridin-3-yl)pyrimidin-4-yl)-3-nitrobenzene-1,2-diol, 3-nitro-5-(2-(5-(trifluoromethyl)pyridin-3-yl)pyrimidin-4-yl)benzene-1,2-diol.

Preferred compounds of the above general formula (I) having as central unit an 1H-pyrrol-2,5-diyl moiety include ethyl 5-(3,4-dihydroxy-5-nitrophenyl)-1-methyl-2-(4-(trifluoromethyl)pyridin-3-yl)-1H-pyrrole-3-carboxylate, ethyl 2-(2-chloro-4,6-dimethylpyridin-3-yl)-5-(3,4-dihydroxy-5-nitrophenyl)-1-methyl-1H-pyrrole-3-carboxylate, 5-(1-methyl-5-(2-methyl-6-(trifluoromethyl)pyridin-3-yl)-1H-pyrrol-2-yl)-3-nitrobenzene-1,2-diol, ethyl 5-(3,4-dihydroxy-5-nitrophenyl)-1-ethyl-2-(6-(trifluoromethyl)pyridin-3-yl)-1H-pyrrole-3-carboxylate, 5-(1-methyl-5-(6-methyl-4-(trifluoromethyl)pyridin-3-yl)-1H-pyrrol-2-yl)-3-nitrobenzene-1,2-diol, 5-(5-(2,6-dimethyl-4-(trifluoromethyl)pyridin-3-yl)-1-methyl-1H-pyrrol-2-yl)-3-nitrobenzene-1,2-diol, 5-(5-(3,5-dichloropyridin-4-yl)-1-methyl-1H-pyrrol-2-yl)-3-nitrobenzene-1,2-diol, 5-(1-methyl-5-(6-methyl-2-phenyl-4-(trifluoro-methyl)pyridin-3-yl)-1H-pyrrol-2-yl)-3-nitrobenzene-1,2-diol, 5-(5-(2-bromo-4,5,6-trimethylpyridin-3-yl)-1-methyl-1H-pyrrol-2-yl)-3-nitrobenzene-1,2-diol, 5-(5-(2-chloro-4,5,6-trimethylpyridin-3-yl)-1-methyl-1H-pyrrol-2-yl)-3-nitrobenzene-1,2-diol, 5-(1-methyl-5-(2-(trifluoromethyl)pyridin-3-yl)-1H-pyrrol-2-yl)-3-nitrobenzene-1,2-diol, 5-(5-(2,5-dichloro-4,6-dimethylpyridin-3-yl)-1-methyl-1H-pyrrol-2-yl)-3-nitrobenzene-1,2-diol, 5-(1-methyl-5-(5-(trifluoromethyl)pyridin-3-yl)-1H-pyrrol-2-yl)-3-nitrobenzene- 1,2-diol, 5-(5-(2-fluoropyridin-3-yl)-1-methyl-1H-pyrrol-2-yl)-3-nitrobenzene-1,2-diol, 5-(5-(2-fluoropyridin-4-yl)-1-methyl-1H-pyrrol-2-yl)-3-nitrobenzene-1,2-diol, ethyl 5-(3,4-dihydroxy-5-nitrophenyl)-2-(6-fluoropyridin-2-yl)-1-methyl-1H-pyrrole-3-carboxylate, 5-(5-(2-chloro-6-methylpyridin-3-yl)-1-methyl-1H-pyrrol-2-yl)-3-nitrobenzene-1,2-diol, 5-(5-(2-bromo-6-methylpyridin-3-yl)-1-methyl-1H-pyrrol-2-yl)-3-nitrobenzene-1,2-diol, 5-(5-(2-bromo-5-chloro-4,6-dimethylpyridin-3-yl)-1-methyl-1H-pyrrol-2-yl)-3-nitrobenzene-1,2-diol. Preferred compounds of the above general formula (I) having as central unit an 2H-tetrazol-2,5-diyl moiety include 3-nitro-5-(2-(4-(trifluoromethyl)pyridin-3-yl)-2H-tetrazol-5-yl)benzene-1,2-diol, 3-nitro-5-(2-(6-(trifluoromethyl)pyridin-3-yl)-2H-tetrazol-5-yl)benzene-1,2-diol, 5-(2-(3,5-dichloropyridin-4-yl)-2H-tetrazol-5-yl)-3-nitrobenzene-1,2-diol, 3-nitro-5-(2-(2-(trifluoromethyl)pyridin-3-yl)-2H-tetrazol-5-yl)benzene-1,2-diol, 3-nitro-5-(2-(5-(trifluoromethyl)pyridin-3-yl)-2H-tetrazol-5-yl)benzene-1,2-diol.

Preferred compounds of the above general formula (I) having as central unit an 1,2,3-thiadiazol-4,5-diyl moiety include 3-nitro-5-(5-(4-(trifluoromethyl)pyridin-3-yl)-1,2,3-thiadiazol-4-yl)benzene-1,2-diol, 5-(5-(2-chloro-4,6-dimethylpyridin-3-yl)-1,2,3-thiadiazol-4-yl)-3-nitrobenzene-1,2-diol, 5-(5-(2-methyl-6-(trifluoromethyl)pyridin-3-yl)-1,2,3-thiadiazol-4-yl)-3-nitrobenzene-1,2-diol, 3-nitro-5-(5-(6-(trifluoromethyl)pyridin-3-yl)-1,2,3-thiadiazol-4-yl)benzene-1,2-diol, 5-(5-(6-methyl-4-(trifluoromethyl)pyridin-3-yl)-1,2,3-thiadiazol-4-yl)-3-nitrobenzene-1,2-diol, 5-(5-(2,6-dimethyl-4-(trifluoromethyl)pyridin-3-yl)-1,2,3-thiadiazol-4-yl)-3-nitrobenzene-1,2-diol, 5-(5-(3,5-dichloropyridin-4-yl)-1,2,3-thiadiazol-4-yl)-3-nitrobenzene-1,2-diol, 5-(5-(6-methyl-2-phenyl-4-(trifluoromethyl)pyridin-3-yl)-1,2,3-thiadiazol-4-yl)-3-nitrobenzene-1,2-diol, 5-(5-(2-bromo-4,5,6-trimethylpyridin-3-yl)-1,2,3-thiadiazol-4-yl)-3-nitrobenzene-1,2-diol, 5-(5-(2-chloro-4,5,6-trimethylpyridin-3-yl)-1,2,3-thiadiazol-4-yl)-3-nitrobenzene-1,2-diol, 3-nitro-5-(5-(2-(trifluoromethyl)pyridin-3-yl)-1,2,3-thiadiazol-4-yl)benzene-1,2-diol, 5-(5-(2,5-dichloro-4,6-dimethylpyridin-3-yl)-1,2,3-thiadiazol-4-yl)-3-nitrobenzene-1,2-diol, 3-nitro-5-(5-(5-(trifluoromethyl)pyridin-3-yl)-1,2,3-thiadiazol-4-yl)benzene-1,2-diol, 5-(5-(2-fluoropyridin-3-yl)-1,2,3-thiadiazol-4-yl)-3-nitrobenzene-1,2-diol, 5-(5-(2-fluoropyridin-4-yl)-1,2,3-thiadiazol-4-yl)-3-nitrobenzene-1,2-diol, 5-(5-(6-fluoropyridin-2-yl)-1,2,3-thiadiazol-4-yl)-3-nitrobenzene-1,2-diol, 5-(5-(2-chloro-6-methylpyridin-3-yl)-1,2,3-thiadiazol-4-yl)-3-nitrobenzene-1,2-diol, 5-(5-(2-bromo-6-methylpyridin-3-yl)-1,2,3-thiadiazol-4-yl)-3-nitrobenzene-1,2-diol, 5-(5-(2-bromo-5-chloro-4,6-dimethylpyridin-3-yl)-1,2,3-thiadiazol-4-yl)-3-nitrobenzene-1,2-diol.

Preferred compounds of the above general formula (I) having as central unit an 1,3-thiazol-2,4-diyl moiety include 3-nitro-5-(2-(4-(trifluoromethyl)pyridin-3-yl)thiazol-4-yl)benzene-1,2-diol, 5-(2-(2-chloro-4,6-dimethylpyridin-3-yl)thiazol-4-yl)-3-nitrobenzene-1,2-diol, 5-(2-(2-methyl-6-(trifluoromethyl)pyridin-3-yl)thiazol-4-yl)-3-nitrobenzene-1,2-diol, 3-nitro-5-(2-(6-(trifluoromethyl)pyridin-3-yl)thiazol-4-yl)benzene-1,2-diol, 5-(2-(6-methyl-4-(trifluoromethyl)pyridin-3-yl)thiazol-4-yl)-3-nitrobenzene-1,2-diol, 5-(2-(2,6-dimethyl-4-(trifluoromethyl)pyridin-3-yl)thiazol-4-yl)-3-nitrobenzene-1,2-diol, 5-(2-(3,5-dichloropyridin-4-yl)thiazol-4-yl)-3-nitrobenzene-1,2-diol, 5-(2-(6-methyl-2-phenyl-4-(trifluoromethyl)pyridin-3-yl)thiazol-4-yl)-3-nitrobenzene-1,2-diol, 5-(2-(2-bromo-4,5,6-trimethylpyridin-3-yl)thiazol-4-yl)-3-nitrobenzene-1,2-diol, 5-(2-(2-chloro-4,5,6-trimethylpyridin-3-yl)thiazol-4-yl)-3-nitrobenzene-1,2-diol, 3-nitro-5-(2-(2-(trifluoromethyl)pyridin-3-yl)thiazol-4-yl)benzene-1,2-diol, 5-(2-(2,5-dichloro-4,6-dimethylpyridin-3-yl)thiazol-4-yl)-3-nitrobenzene-1,2-diol, 3-nitro-5-(2-(5-(trifluoromethyl)pyridin-3-yl)thiazol-4-yl)benzene-1,2-diol, 5-(2-(2-fluoropyridin-3-yl)thiazol-4-yl)-3-nitrobenzene-1,2-diol, 5-(2-(2-fluoropyridin-4-yl)thiazol-4-yl)-3-nitrobenzene-1,2-diol, 5-(2-(6-fluoropyridin-2-yl)thiazol-4-yl)-3-nitrobenzene-1,2-diol, 5-(2-(2-chloro-6-methylpyridin-3-yl)thiazol-4-yl)-3-nitrobenzene-1,2-diol, 5-(2-(2-bromo-6-methylpyridin-3-yl)thiazol-4-yl)-3-nitrobenzene-1,2-diol, 5-(2-(2-bromo-5-chloro-4,6-dimethylpyridin-3-yl)thiazol-4-yl)-3-nitrobenzene-1,2-diol.

As used herein, the term 'compound of the invention' or 'compounds of the invention', includes a compound of general formula I as defined above, and includes any of the preferred compounds listed above.

The most preferred example of a compound according to the general formula I is 5-[3-(2,5-dichloro-4,6-dimethylpyridin-3-yl)-[1,2,4]oxadiazol-5-yl]-3-nitrobenzene-1,2-diol, henceforth designated as compound A.

In one preferred embodiment, compounds of the general formula I wherein the central unit consists of a 1,2,4-oxadiazo-3,5-diyl-moiety can be prepared by a process wherein a compound of the general formula IIA, IIB or IIC,

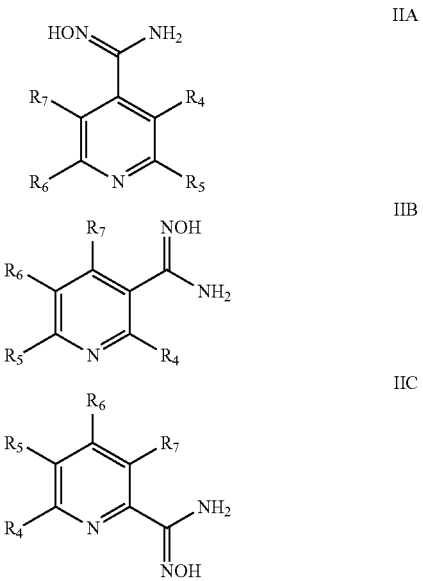

wherein $R_4$, $R_5$, $R_6$ and $R_7$ are defined as in the general formula I, is subjected to a cyclisation reaction comprising condensation and dehydration with a compound of the general formula III,

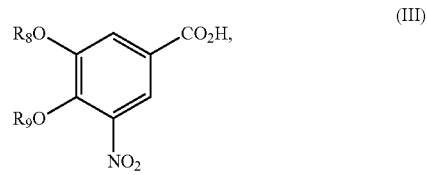

wherein $R_8$ and $R_9$ independently from each other represent hydrogen or suitable protective groups for aromatic hydroxyl groups, under conditions suitable to produce oxadiazole derivatives, followed by removal of the hydroxyl protecting groups to provide the compounds of general formula I.

Suitable protective groups for aromatic hydroxyl groups are well known in the art. Examples of suitable protective groups for aromatic hydroxyl groups include methyl, ethyl, isopropyl, benzyl, 4-methoxybenzyl, methoxymethyl, benzyloxymethyl, methoxyethoxymethyl, tetra-hydropyranyl, phenacyl, allyl, trimethylsilyl, tert-butyldimethylsilyl, benzyloxycarbonyl, tert-butoxycarbonyl, ester, sulphonate, carbamate, phosphinate, acetal and ketal derivatives.

In a preferred embodiment, one of the groups $R_8$ and $R_9$ is hydrogen and the other is methyl. In a particularly preferred embodiment, $R_8$ represents methyl and $R_9$ represents hydrogen.

In an alternative preferred embodiment, the protective groups $R_8$ and $R_9$ are replaced with hydrogen or a group which is hydrolysable under physiological conditions. The protective groups $R_8$ and $R_9$ may be removed independently from each other in separate reaction steps or they may be removed in the same reaction step. Likewise, the insertion of a group which is hydrolysable under physiological conditions may take place either in the same or in a subsequent reaction step.

In the present invention, conditions suitable to produce oxadiazole derivatives comprise conditions which give the oxadiazole derivative in high yield and purity. Preferably, the yield of the desired oxadiazole derivative is at least 70%, more preferably 75 to 99%, even more preferably 80 to 97%, and most preferably 85 to 95%. Preferably, the purity of the desired oxadiazole derivative is at least 90%, more preferably at least 95%, even more preferably at least 99%, and most preferably at least 99.5%. Following the teaching of the present invention the skilled person can routinely determine the most suitable reaction conditions in order to optimize the yield and purity of the oxadiazole. Parameters to be taken into consideration by the skilled person include, but are not limited to, reagents effecting the condensation and dehydration agents, choice of protective groups $R_8$ and $R_9$, solvent system, reaction temperature and reaction time and solubility of reagents.

The compound of general formula III requires activation before condensation with a compound of formula IIA-IIC. Suitable reagents for activation of the compound of formula III include 1,1-carbonyldiimidazole, thionyl chloride, sulfonylchloride, N,N'-dicyclohexyl-carbodiimide, 1-hydroxybenzotriazole and N-(3-dimethylaminopropyl)-N'-ethylcarbodiimide, phosgene, $PCl_3$, $POCl_3$, $PCl_5$, anhydrides, trichlorotriazine and chlorodi-methoxytriazine and the like. Particularly preferable are 1,1-carbonyldiimidazole and thionyl chloride. In some cases, the same reagents can be employed to effect the cyclisation step, which consists of condensation and dehydration. Alternative reagents to effect condensation and/or dehydration include pyridine and tetrabutylammonium fluoride. Preferably the dehydration can be effected by thermal heating of the reaction mixture in conjunction with the aforementioned reagents.

The compound of general formula III can be activated with an excess of a reagent such as thionyl chloride in a suitable solvent or without the need for additional solvent. If preferred, the excess reagent can then be removed, e.g. by distillation, and replaced with a solvent and another reagent such as pyridine to effect the condensation and dehydration steps. Preferred solvent systems for activating the compound of general formula III, and cyclisation with compounds of general formulas IIA-IIC are dipolar aprotic solvents including dimethylformamide, dimethylsulfoxide, dimethylacetamide and N-methylpyrrolidinone. Particularly preferable are dimethylsulfoxide and dimethylacetamide.

Suitable reaction temperatures and reaction times depend on the reactivity of the utilized reagents for effecting condensation and dehydration. Preferably, the reaction temperature is in the range of 0° C. to the boiling point of the utilized solvent system, more preferably in the range of 20 to 150° C., and most preferably in the range of 25 to 120° C. Preferably, the reaction time is in the range of 30 minutes to 24 hours, more preferably in the range of 1 hour to 18 hours, and most preferably 2 to 6 hours.

In an alternative preferred embodiment, the condensation and dehydration reaction is carried out in the presence of an organic or inorganic base. Suitable preferred bases include triethyl-amine, tributylamine, 2,6-lutidine, N-methylmorpholine, pyridine, imidazole, N-methylimidazole and 4-dimethylaminopyridine. Particularly preferred bases include pyridine, N-methylimidazole and 4-dimethylaminopyridine.

In a preferred embodiment of the present invention, the condensation and dehydration are conducted in two separate reaction steps. In this particular embodiment, different condensation and dehydration agents and solvent systems may be utilized to optimize yield and purity of the obtained product.

In an alternative preferred embodiment of the present invention, the condensation and dehydration are conducted sequentially in the same vessel without isolation of intermediates. In this particular embodiment, the reagents effecting the condensation and dehydration can be the same or different but are preferably identical.

The amount of reagents effecting the condensation and dehydration are not critical. Typical amounts of reagents effecting the condensation and dehydration include at least an amount of 1 mol, preferably 2.1 mol to 5 mol, more preferably 2.2 to 4 mol, and most preferably 2.3 mol to 3 mol, per mol pyridine derivative. In cases in which the reagents effecting the condensation and dehydration also serves as solvent or co-solvent, the excess amount may be much higher.

In another aspect of the invention, compounds of formula IIA, IIB and IIC are prepared by reacting compounds of the general formula IVA, IVB or IVC,

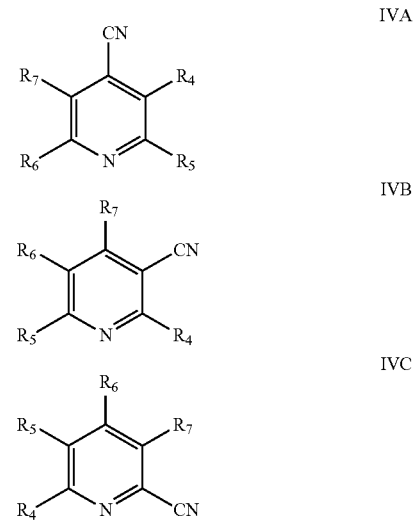

with hydroxylamine in the presence of a chelating agent under suitable reaction conditions.

In the present invention, suitable reaction conditions of the above reaction comprise conditions which give the amidoxime derivative in high yield and purity. Preferably, the yield of the desired amidoxime derivative is at least 70%, more preferably 72 to 95%, even more preferably 75 to 90%, and most preferably 78 to 85%. Preferably, the purity of the desired amidoxime derivative is at least 90%, more preferably at least 95%, even more preferably at least 96%, and most preferably at least 97%. Following the teaching of the present invention the skilled person can routinely determine the most suitable reaction conditions in order to optimize the yield and purity of the amidoxime. Parameters to be taken into consideration by the skilled person include, but are not limited to, amount of hydroxylamine, choice of catalyst, nature of substituents $R_4$-$R_7$, solvent system, reaction temperature and reaction time and solubility of reagents.

The preferred amount of hydroxylamine is in the range of equimolar amounts to a 50-fold excess to the pyridine derivative. Preferably, the amount of hydroxylamine is in the range of a 1.2-fold to 20-fold excess, more preferably 1.5-fold to 10-fold excess and most preferably to 3-fold to 5-fold excess.

Preferred chelating agents include 8-hydroxyquinoline, ortho-phenanthroline and hydrates and derivatives thereof. The preferred amount of chelating agent is in the range 0.1-10 mol %, more preferably 0.5-5 mol %, more preferably 0.75-3 mol % and most preferably 1-1.5 mol %.

The solvent system is not particularly limited and includes water, alcohols such as methanol, ethanol or isopropanol, ethers such as THF or 1,4-dioxane, and dipolar aprotic solvents, such as dimethylsulfoxide and the like or mixtures of these solvents.

Preferably, the reaction temperature is in the range of 0° C. to the boiling point of the utilized solvent system, more preferably in the range of 20 to 100° C., and most preferably in the range of 40 to 80° C. Preferably, the reaction time is in the range of 30 minutes to 24 hours, more preferably in the range of 1 hour to 18 hours, and most preferably 2 to 8 hours.

The following reaction scheme 1 depicts example how to produce a compound of the general formula JIB from a compound of the general formula IVB:

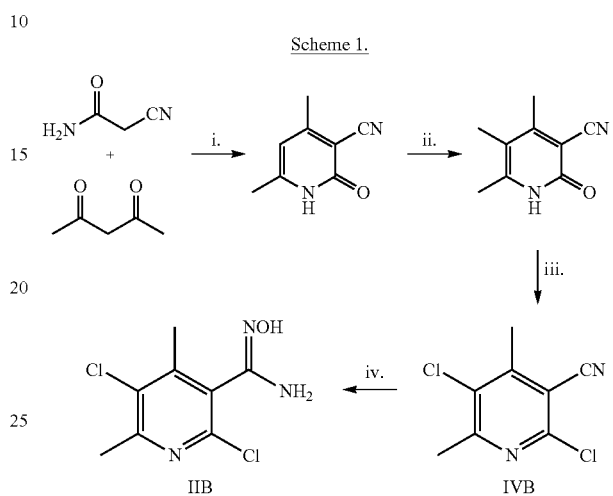

Reagents: i. Piperidine, ethanol, reflux; ii. SO$_2$Cl$_2$, CCl$_4$, reflux; iii. POCl$_3$, 120° C., 18 h; iv. 50% H$_2$NOH, MeOH—H$_2$O, 1.25 mol % 1,10-phenanthroline hydrate.

The following reaction scheme 2 depicts an example how to produce certain compounds of general formula III:

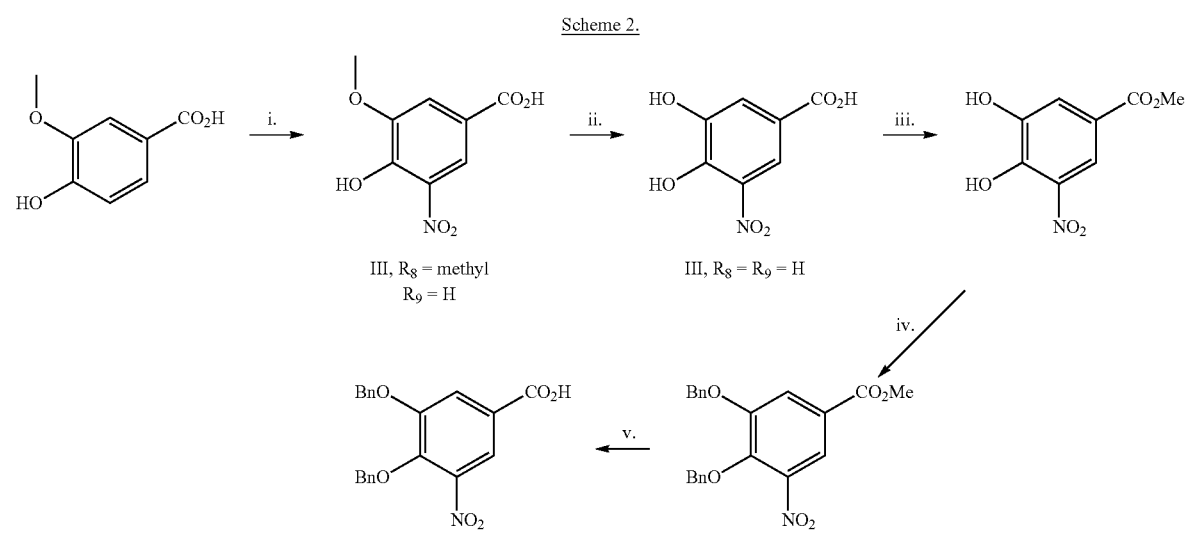

Reagents: i. 65% HNO$_3$, AcOH; ii. 48% HBr (aq), 140° C.; iii. MeOH, HCl(g); iv. BnBr, K$_2$CO$_3$, CH$_3$CN, reflux; v. 3N NaOH, MeOH/H$_2$O.

The following reaction scheme 3 depicts an example how to produce the compound A, by activation of a compound according to general formula III followed by cyclisation involving condensation with a compound according to formula IIB, dehydration and deprotection of the methyl residue protecting the hydroxyl group;

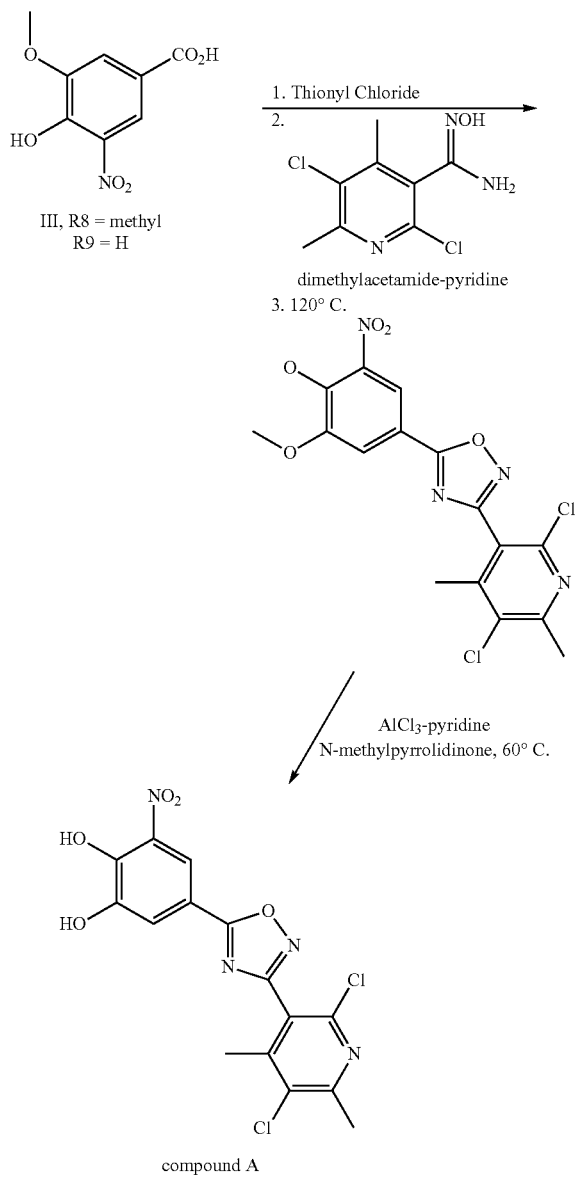

Scheme 3. Preparation of compound A compound A

The above depicted general reaction principles are exemplified in Examples 17 and 18.

Compounds of the above general formula I having other central units than the 1,2,4-oxadiazo-3,5-diyl-moiety can be readily prepared by the skilled person as is outlined in the processes employed in the Examples.

Another embodiment of the present invention relates to a compound of the invention for use as an active ingredient in a pharmaceutical composition.

A further embodiment of the present invention relates to a pharmaceutical composition comprising a compound of the invention and a pharmaceutically acceptable excipient.

The compounds of the invention may be present in the pharmaceutical composition in the form of pharmacologically acceptable salts or esters thereof. Suitable pharmacologically acceptable counter ions are known to the art. Prodrugs of the compounds may also be used to alter the therapeutic profile of the active compound.

For the preparation of pharmaceutical compositions or preparations of the invention, inert pharmacologically acceptable carriers are admixed with the active compounds. The pharmaceutically acceptable carriers may be either solid or liquid. Solid form preparations include powders, tablets, dispersible granules and capsules. A solid carrier can be one or more substances which may also act as diluents, flavouring agents, solubilisers, lubricants, suspending agents, binders or tablet disintegrating agents; it may also be an encapsulating material.

Preferably, the pharmaceutical preparation is in unit dosage form, e.g. packaged preparation, the package containing discrete quantities of preparation such as packaged tablets, capsules and powders in vials or ampoules.

In another embodiment of the present invention there is provided a method for the treatment of diseases, said methods comprising the step of administering an effective dose of a pharmaceutical composition of the invention to a subject in need thereof.

Diseases which may be treated by administration of a pharmaceutical composition of the invention include central and peripheral nervous system disorders where a reduction in the O-methylation of catecholamines may be of therapeutic benefit, namely movement disorders such as restless leg syndrome, Parkinson's disease and disorders or pathological states involving Parkinsonism and Parkinson's symptoms; gastrointestinal disturbances, oedema formation states and hypertension.

According to another aspect of the invention there is provided a method of reducing COMT activity in a subject, comprising the step of administering an effective amount of a compound of formula I. Preferably the COMT inhibition is reduced over 24 to 48 hours.

According to further aspect of the invention there is provided a method of increasing levels of L-DOPA in the brain or plasma of a subject, comprising the step of administering an effective amount of a compound of formula I. Preferably the L-DOPA levels are increased over 24 to 48 hours.

According to further aspect of the invention there is provided a method of increasing bioavailability of L-DOPA in the brain or plasma of a subject, comprising the step of administering an effective amount of a compound of formula I. Preferably the L-DOPA bioavailability is increased over 24 to 48 hours.

According to yet further aspect of the invention there is provided a method of decreasing levels of 3-O-methyl-L-DOPA (3-OMD) in the brain or plasma of a subject, comprising the step of administering an effective amount of a compound of formula I. Preferably the 3-OMD levels are decreased over 24 to 48 hours.

Preferably the step of administering is from about twice every day to about once every other day, preferably once per day.

As used herein, the term treatment and variations such as 'treat' or 'treating' refer to any regime that can benefit a human or non-human animal. The treatment may be in respect of an existing condition or may be prophylactic (preventative treatment). Treatment may include curative, alleviation or prophylactic effects.

The dosages may be varied depending on the requirement of the patient, the severity of the disease, the particular compound being employed, and the administration route. For convenience, the total daily dosage may be divided and administered in portions throughout the day. Determination of the proper dosage for a particular situation is within the skill of those in the medical art.

Such doses may be administered in any manner useful in directing the active compounds to the target site of the subject, namely the central and peripheral nervous system. Suitable routes of administration include orally, via implants, parentally (including intravenous, intraperitoneal, intraarticular and subcutaneous injections), rectally, intranasally, topically, ocularly (via eye drops), vaginally, and transdermally.

The compounds of the invention are preferably used for the preparation of a medicament for the prevention or treatment of a disorder or pathological state according to a specified dosing regimen.

Suitable dosing regimens comprise regimens having a dosing periodicity ranging from about twice a day to about once every other day.

As used herein, the term dosing periodicity refers to the number of effective doses of a compound of general formula I given in the specified time interval.

Preferably, the dosing periodicity is selected from twice daily, once daily and once every other day.

In case of a dosage periodicity of twice daily, the doses can be administered in dosing intervals of 8 to 16 hours, wherein the individual two dosing intervals should accumulate to about 24 hours. Suitable non-limiting starting points for dosing intervals comprise the morning, mid-day, noon, afternoon, evening, and midnight. For example, a twice daily dosing regimen according to the invention can require the administration of a dose at 8.00 in the morning and another dose at 17.00 in the afternoon (in this case, the dosing intervals are 11 hours and 13 hours and add up to about 24 hours). Preferably, the time interval between two doses is about 12 h.

In case of a dosage periodicity of once daily, the doses can be administered in dosing intervals of about 24 hours. Suitable non-limiting starting points for dosing intervals comprise the morning, mid-day, noon, afternoon, evening, and midnight. For example, a once daily dosing regimen according to the invention can require the administration of a dose at 8.00 in the morning and another dose at 8.00 on the next morning (in this case, the dosing interval is about 24 h).

In case of a dosage periodicity of once every other day, the doses can be administered in dosing intervals of 18 to 30 hours, wherein the individual two dosing intervals should accumulate to about 48 hours. Suitable non-limiting starting points for dosing intervals comprise the morning, mid-day, noon, afternoon, evening, and midnight. For example, a once every other day daily dosing regimen according to the invention can require the administration of a dose at 8.00 in the morning on the first day and another dose at 13.00 in the afternoon of the second day (in this case, the dosing intervals are 29 hours and 19 hours and add up to about 48 hours). Preferably, the time interval between two doses is about 24 h.

In the present invention, effective daily doses of compounds of general formula I are in the range of 1-1000 mg/day, more preferably 2 to 500 mg/day, even more preferably 3 to 250 mg/day, and most preferably 5-100 mg/day.

It is preferred that individual dosage units of compounds of general formula I are in the range of 1-500 mg, more preferably 2 to 300 mg/day, even more preferably 3 to 100 mg/day, and most preferably 5-50 mg, wherein the daily dosage can differ depending on the time of administration. For instance, in a twice daily dosing regimen, it is possible to administer a dose containing 11/24 of the daily dose of a compound of general formula I at 8.00 in the morning to and another dose containing 13/24 of the daily dose of a compound of general formula I at 17.00 in the afternoon.

As used herein, the term "dosage unit" refers to the individual pharmaceutical formulation, e.g. a tablet, containing the compound of general formula I to be administered to a patient at that time of the dosage regimen.

Preferably the subject being treated with the compound of general formula I is also receiving therapy with L-DOPA and/or an aromatic L-amino acid decarboxylase inhibitor (AADC), such as a DOPA decarboxylase inhibitor. Suitable inhibitors are carbidopa and benserazide.

The compounds of general formula I, L-DOPA and AADC may be administered separately or in any combination. They may be administered concomitantly (for example, simultaneously) or sequentially and with the same or differing dosing periodicity. For example, the compounds of the general formula I can be concomitantly or sequentially administered with L-DOPA. In case of concomitant administration it is also possible to combine both active ingredients in one pharmaceutical formulation.

A further embodiment of the present invention relates to the use of the compounds of the invention or their pharmaceutically acceptable salts or esters for the treatment of a pathological state or disease in a human or non-human animal.

A yet further embodiment of the present invention relates to the use of compounds of the invention or their pharmaceutically acceptable salts or esters in the preparation of a pharmaceutical composition for treating such pathological states or diseases.

It is also possible to use prodrugs of compounds of the invention in order to alter the therapeutic profile of the active compound.

The present invention also relates to a package comprising a pharmaceutical composition comprising a compound of the general formula I in combination with instructions to administer said composition with a dosing regimen having a dosing periodicity ranging from about twice a day to about once every other day, preferably once per day.

The package may also include L-DOPA and/or an AADC inhibitor such as benserazide or to carbidopa.

Preferred features of each embodiment or aspect of the invention are also applicable to each other embodiment or aspect of the invention mutatis mutandis, unless the context demands otherwise. For example, where a composition of the invention is administered preferably once per day, the administration step in a method of treatment may also be preferably once per day.

The COMT activity is evidenced by the ability to methylate adrenaline to metanephrine, as previously described (Vieira-Coelho, M. A., Soares-da-Silva, P., Brain Res, 1999, 821, 69-78). An experimental setup is described below: Aliquots of 0.5 ml of liver homogenates were preincubated for 20 min with 0.4 ml of phosphate buffer (5 mM); thereafter, the reaction mixture was incubated for 10 min with adrenaline (500 µM; 0.1 ml) in the presence of a saturating concentration of S-adenosyl-L-methionine, the methyl donor (250 µM). The incubation medium also contained pargyline (100 µM), $MgCl_2$ (100 µM) and EGTA (1 mM). The preincubation and incubation were carried out at 37° C. under conditions of light protection with continuous shaking and without oxygenation. At the end of the incubation period the tubes were transferred to ice and the reaction was stopped by the addition of 200 µl of 2 M perchloric acid. The samples were then centrifuged (200×g, 4 min, 4° C.), and 500 µl aliquots of the supernatant, filtered on 0.22 µm pore size Spin-X filter tubes (Costar) were used for the assay of metanephrine by high pressure liquid chromatography with electrochemical detection.

In experiments designed to evaluate the effects of test compounds upon liver COMT, test compounds (in 5% carboxymethylcellulose) were given by gastric tube to overnight fasted mice. Thereafter, at defined intervals, livers were removed and used to determine COMT activity as described above.

Cell toxicity is evidenced by the method described by Pedrosa and Soares-da-Silva (Br. J. Pharmacol., 137, 1 1305-1313, 2002). An experimental setup is described below: Neuro 2A mouse neuroblastoma cells were seeded in 96-well plates in 200 µL per well of culture medium for cell attachment (CMA), under a $CO_2$/air (5%/95%) humidified atmosphere at 37° C. Controls of the test system prior to incubations consisted in a morphological control (light microscopy) of the cultured cells: attachment, spreading and density. Five days after seeding (24 h after cells become confluent), the test compounds were incubated for 24 h with cultured cells. Cultures with no test article or ethanol were run in parallel as negative and positive controls. All incubations contained the same percentage of solvent needed for the test compound.

Cell viability is evidenced by measuring viability using calcein-AM (Molecular Probes, Eugene, Oreg., USA). The membrane permeant calcein-AM, a nonfluorescent dye, is taken up and converted by intracellular esterases to membrane impermeant calcein, which emits green fluorescence. An experimental setup is described below: After treatment with test article or vehicle for 24 h, cells are washed twice with Hanks' medium (medium composition, in mM: NaCl 137, KCl 5, $MgSO_4$ 0.8, $Na2HPO_4$ 0.33, $KH_2PO_4$ 0.44, $CaCl_2$ 0.25, $MgCl_2$ 1.0, Tris HCl 0.15 and sodium butyrate 1.0, pH=7.4) and loaded with 2 µM calcein-AM in Hanks' medium, at room temperature for 30 min. Fluorescence is measured at 485 nm excitation and 530 nm emission wavelengths in a multiplate reader. To determine minimum staining for calcein-AM ($calcein_{min}$), eight wells were treated with ethanol 30 min before calcein-AM addition. The percent viability is then calculated as [($calcein_{sample}$–$calcein_{min}$)/($calcein_{control}$–$calcein_{min}$)]×100.

Conclusion

The compounds of the invention are promising candidates for drug therapy as is evidenced by their potential to act as COMT inhibitors exhibiting balanced properties of bioactivity, bioavailability and safety over a long time period.

BRIEF DESCRIPTION OF THE FIGS. 1 TO 3

FIG. 1. Effect of compound A and tolcapone (both at 3 mg/kg) on liver COMT activity at 0.5, 1, 3, 6, 9 and 24 h after the administration of either COMT inhibitor. Symbols represent means±SD of 5 experiments per group. Significantly different from corresponding controls values (* $P<0.05$).

Figure 2:
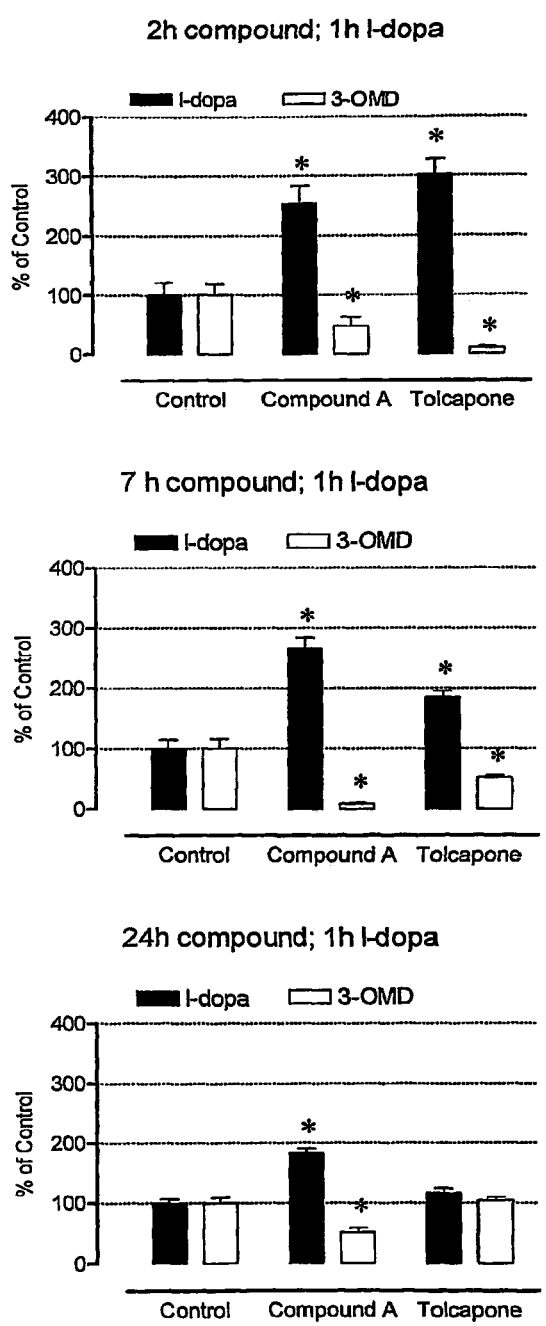

FIG. 2. Effect of compound A and tolcapone (both at 3 mg/kg) on plasma levels of L-DOPA and 3-O-methyl-L-DOPA (3-OMD) in rats treated with L-DOPA (12 mg/kg) plus benserazide (3 mg/kg) at 2, 7 and 24 h after the administration of either COMT inhibitor. Columns represent means±SD of 5 experiments per group. Significantly different from corresponding controls values (* $P<0.05$).

Figure 3:
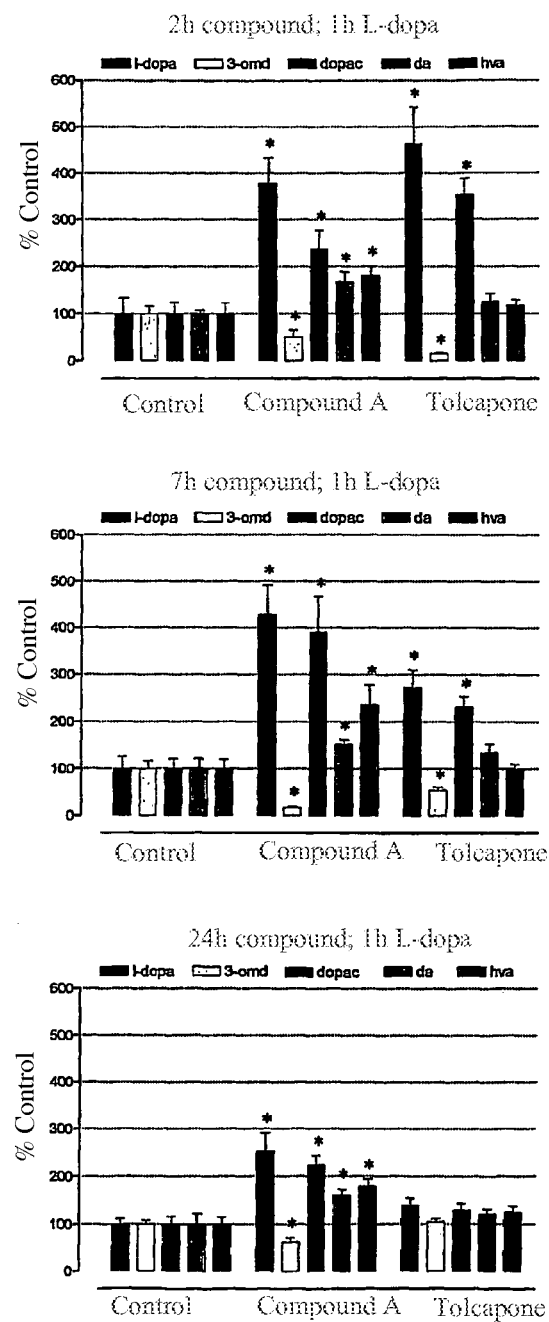

FIG. 3. Effect of compound A and tolcapone (both at 3 mg/kg) on brain levels of L-DOPA, 3-O-methyl-L-DOPA (3-OMD), dopamine, DOPAC and HVA in rats treated with L-DOPA (12 mg/kg) plus benserazide (3 mg/kg), at 2, 7 and 24 h after administration of either COMT inhibitor. Columns represent means±SD of 5 experiments per group. Significantly different from corresponding controls values (* $P<0.05$).

MATERIALS AND METHODS OF BIOLOGICAL ASSAYS

Assay of COMT Activity

Livers from 60 day old male Wistar rats weighing 240-260 g (Harlan-Interfauna Ibérica, Barcelona, Spain), kept two per cage under controlled environmental conditions (12 h light/dark cycle and room temperature 24° C.) were used in all experiments. After decapitation, the organs were immediately removed and homogenised in 5 mM phosphate buffer of pH 7.8. COMT activity was evaluated by the ability to methylate adrenaline to metanephrine. Aliquots of 0.5 ml of liver homogenates were preincubated for 20 min with 0.4 ml of phosphate buffer (5 mM); thereafter, the reaction mixture was incubated for 15 min with epinephrine (2000 µM; 0.1 ml) in the presence of a saturating concentration of S-adenosyl-L-methionine (500 µM), the methyl donor; the incubation medium contained also pargyline (100 µM), $MgCl_2$ (100 µM) and EGTA (1 mM). The preincubation and incubation were carried out at 37° C. under conditions of light protection with continuous shaking and without oxygenation.

In experiments designed to evaluate the oral bioavailability of test substances, compounds were given by gastric tube to overnight fasted rats. Thereafter, at defined intervals, animals were killed by decapitation and livers removed and used to determine COMT activity as described above. At the end of the incubation period (5 min) the tubes were transferred to ice and the reaction was stopped by the addition of 200 µl of 2 M perchloric acid. The samples were then centrifuged (200×g, 4 min, 4° C.), and 500 µl aliquots of the supernatant, filtered on to 0.22 µm pore size Spin-X filter tubes (Costar) were used for the assay of metanephrine. The assay of metanephrine was carried out by means of high pressure liquid chromatography with electrochemical detection. The lower limits for detection of metanephrine ranged from 350 to 500 fmol (0.5 to 1.0 pmol/mg protein/h).

Levels of L-DOPA and its Derivatives in Whole Brain and Plasma

Rats fasted overnight were administered orally with tolcapone and compounds of general formula I (all at 3 mg/kg) or vehicle (0.5% carboxymethylcellulose, 4 ml/kg). One, 6 or 23 h later, rats were administered orally with L-DOPA (12 mg/kg) plus benserazide (3 mg/kg) or with vehicle (0.5% carboxymethylcellulose, 4 ml/kg). One hour later rats were anaesthetised with sodium pentobarbitone (60 mg/kg, i.p.), blood was collected through the vena cava and the whole brain was quickly removed. Brains were stored in perchloric acid 0.2 M for subsequent assay of L-DOPA, 3-O-methyl-L-DOPA, dopamine, DOPAC and HVA. Blood samples were centrifuged for 15 min at 3,000 g (4° C.) and the plasma samples were stored at −80° C. till the assay of L-DOPA and 3-O-methyl-L-DOPA. All animals interventions were performed in accordance with the European Directive number 86/609, and the rules of the "Guide for the Care and Use of Laboratory Animals", 7th edition, 1996, Institute for Laboratory Animal Research (ILAR), Washington, D.C.

Assay of L-DOPA and Catechol Derivatives

L-DOPA, 3-O-methyl-L-DOPA, dopamine and metabolites (DOPAC and HVA) in dialysate samples were assayed by HPLC with electrochemical detection, as previously described (Soares-da-Silva et al., Brain Res. 2000; 863:293-

297). In brief, aliquots of 20 μl were injected into the chromatograph. The chromatographic system consisted of a pump (Gilson 307) and a stainless steel 5 μm ODS2 column (Biophase; Bioanalytical Systems, West Lafayette, Ind.) of 25 cm length and 4.6 mm diameter; samples were injected by means of an automatic sample injector (Gilson 231) connected to a Gilson dilutor (Gilson 401). The mobile phase was a degassed solution of citric acid 0.1 mM; sodium octylsulphate 0.5 mM; sodium acetate 0.1 M; $Na_2EDTA$ 0.17 mM; dibutylamine 1 mM and methanol (10% v/v), adjusted to pH 3.5 with PCA 2 M and pumped at a rate of 1.0 ml $min^{-1}$. The detection was carried out electrochemically with a glassy carbon electrode, an Ag/AgCl reference electrode and an amperometric detector (Gilson 142); the detector cell was operated at 0.75 V. The current produced was monitored using the Gilson Unipoint HPLC software. The lower limit of detection of dopamine, DOPAC and HVA ranged from 350 to 1000 fmol.

Biological Results

Compound A was found to be a potent inhibitor of liver COMT, the maximal inhibitory effect being achieved within 6 h after their oral administration (FIG. 1). The maximal inhibitory effect of tolcapone was observed within 30 min after administration (FIG. 1). Nine hours after administration, tolcapone produces minimal inhibitory effects, whereas compound A is still capable of inhibiting COMT activity by 90% of control levels (FIG. 1). As shown in FIG. 1, 24 hours after administration, compound A maintains inhibition of liver COMT at 60% of control levels, whereas tolcapone is already almost devoid of COMT inhibitory properties at this time.

FIG. 2 shows levels of L-DOPA and 3-O-methyl-L-DOPA (3-OMD) in plasma of rats treated with L-DOPA plus benserazide at 2, 7 and 24 h after the administration of tolcapone and compound A (both at 3 mg/kg). L-DOPA plus benserazide were administered 1 h before collection of blood samples. This time-point was chosen because it represented the $T_{max}$ for L-DOPA. As can be observed, compound A produced significant increases in plasma L-DOPA accompanied by marked decrease in circulating 3-O-methyl-L-DOPA, this being identical at all pre-treatment times with compound A (1, 7 and 24 h). Plasma levels of L-DOPA and 3-O-methyl-L-DOPA not affected when tolcapone was administered 24 h in advance. Significant changes on L-DOPA and 3-O-methyl-L-DOPA plasma levels by tolcapone were only observed at 2 and 7 h after the administration of the compound.

FIG. 3 shows levels of L-DOPA, 3-O-methyl-L-DOPA, DOPAC, dopamine and HVA in the brain of rats treated with L-DOPA plus benserazide at 2, 7 and 24 h after the administration of tolcapone and compound A (3 mg/kg). L-DOPA plus benserazide were administered 1 h before collection of brain samples. This time-point was chosen because it represented the $T_{max}$ for L-DOPA. As can be observed, compound A produced significant increases in brain L-DOPA, dopamine and DOPAC accompanied by marked decrease in brain 3-O-methyl-L-DOPA, this being identical at all pre-treatment times with compounds A (1, 7 and 24 h). Brain levels of L-DOPA, dopamine, DOPAC and 3-O-methyl-L-DOPA were not affected when tolcapone was administered 24 h in advance. Significant changes on L-DOPA, dopamine, DOPAC and 3-O-methyl-L-DOPA brain levels by tolcapone were only observed at 2 and 7 h after the administration of the compound.

The invention will now be described with reference to the following examples, which are not intended to limit the scope of the application.

EXAMPLE 1

As an example of a compound of the general formula (I) having a 1,3,4-oxadiazol-2,5-diyl moiety as central unit 3-nitro-5-[5-(2-trifluoromethyl-pyridin-3-yl)-[1,3,4]oxadiazol-2-yl]-benzene-1,2-diol was prepared by the following procedure:

a) A mixture of 3,4-dimethoxy-5-nitrobenzoic acid (0.53 g, 2.34 mmol) and 1,1-carbonyldiimidazole (0.42 g, 2.59 mmol) was heated in tetrahydrofuran (10 mL) at reflux for three hours and then cooled to room temperature. 2-Trifluoromethyl-nicotinic acid hydrazide (0.53 g, 2.57 mmol) was added in one portion and the yellowish mixture was stirred at reflux overnight and then allowed to cool to room temperature. The mixture was poured onto cold water (100 mL) and the copious precipitate was filtered off, washed with water and dried to give 2-trifluoromethyl-nicotinic acid N'-(3,4-dimethoxy-5-nitro-benzoyl)-hydrazide (0.71 g, 73%).

b) A suspension of 2-trifluoromethyl-nicotinic acid N'-(3,4-dimethoxy-5-nitro-benzoyl)-hydrazide (0.60 g, 1.44 mmol) in phosphorus oxychloride (10 mL) was stirred at 130° C. for three hours, becoming a pale yellow solution. The mixture was allowed to cool to room temperature and then poured onto ice-water (200 mL). The white precipitate was filtered off, washed with water and dried to give 2-(3,4-dimethoxy-5-nitrophenyl)-5-(2-(trifluoromethyl)pyridin-3-yl)-1,3,4-oxadiazole, 0.48 g (84%).

c) A suspension of 2-(3,4-dimethoxy-5-nitrophenyl)-5-(2-(trifluoromethyl)pyridin-3-yl)-1,3,4-oxadiazole (0.289 g, 0.73 mmol) in a mixture of 48% hydrobromic acid (5 mL) and 30% hydrogen bromide in acetic acid (5 mL) was heated at 140° C. overnight and then allowed to cool to room temperature. After evaporation to dryness under reduced pressure, toluene (10 mL) was added to the residue and re-evaporated under reduced pressure. The resulting solid was recrystallised from isopropanol to give 3-nitro-5-[5-(2-trifluoromethyl-pyridin-3-yl)-[1,3,4]oxadiazol-2-yl]-benzene-1,2-diol as a yellow solid, 0.183 g, (68%).

EXAMPLE 2

As an example of a compound of the general formula (I) having a pyrimidin-2,4-diyl moiety as central unit 3-nitro-5-(2-(2-(trifluoromethyl)pyridin-3-yl)pyrimidin-4-yl)benzene-1,2-diol was prepared by the following procedure:

a) A stirred suspension of 1-(3,4-dimethoxy-5-nitro-phenyl)-3-dimethylamino-propen-1-one (0.28 g, 1.0 mmol), 2-(trifluoromethyl)nicotinimidamide (0.283 g, 1.5 mmol) and potassium tert-butoxide (0.17 g, 1.5 mmol) in absolute ethanol (5 mL) was heated to 80° C. in a sealed tube for one hour and then allowed to cool to room temperature. The mixture was poured onto cold water (100 mL) and the resulting precipitate was filtered off, washed with water and dried to give 4-(3,4-dimethoxy-5-nitrophenyl)-2-(2-(trifluoromethyl)pyridin-3-yl)pyrimidine, 0.296 g (73%).

b) A suspension of 4-(3,4-dimethoxy-5-nitrophenyl)-2-(2-(trifluoromethyl)pyridin-3-yl)pyrimidine (0.239 g, 0.59 mmol) in 48% hydrobromic acid (5 mL) was stirred at 140° C. for four hours and then allowed to cool to room temperature. The mixture was poured onto ice-water (100 mL) and the resulting filtrate was filtered off, washed with water and dried to give 3-nitro-5-(2-(2-(trifluoromethyl)pyridin-3-yl)pyrimidin-4-yl)benzene-1,2-diol, 0.201 g (90%).

EXAMPLE 3

As an example of a compound of the general formula (I) having a benzene-1,3-diyl moiety as central unit 5-nitro-3'-

(6-(trifluoromethyl)pyridin-2-yl)biphenyl-3,4-diol was prepared by the following procedure:

a) To a stirred solution of 4-benzyloxy-3-methoxyphenylboronic acid (1.0 g, 3.87 mmol) and 2-(3-bromophenyl)-6-(trifluoromethyl)pyridine (1.063 g, 3.52 mmol) in toluene (10 mL) and ethanol (1 mL) at room temperature under argon was added 2 N aqueous sodium carbonate solution (5.41 mL, 10.82 mmol) followed by tetrakis(triphenylphosphine)palladium (0.22 g, 0.19 mmol). The resulting mixture was stirred at 90° C. for two hours and then allowed to cool to room temperature. The phases were separated and the aqueous phase was extracted with toluene (5 mL). The combined organic phases were washed with water and brine, then dried over anhydrous sodium sulphate and filtered. Evaporation of the solvent left a brown oil that was chromatographed over silica gel (petroleum ether/ethyl acetate, 9:1) to give 2-(4'-(benzyloxy)-3'-methoxybiphenyl-3-yl)-6-(trifluoromethyl)pyridine as a clear oil, 1.072 g (70%).

b) To a solution of 2-(4'-(benzyloxy)-3'-methoxybiphenyl-3-yl)-6-(trifluoromethyl)pyridine (1.061 g, 2.44 mmol) in dichloromethane (20 mL) cooled in an ice-water bath was added a 30% solution of hydrogen bromide in acetic acid (4 mL, 20 mmol) dropwise. The resulting solution was allowed to stir at room temperature for six hours then poured onto ice-water (100 mL). The phases were separated and the aqueous phase was extracted with dichloromethane (10 mL). The combined organic layers were washed with water and brine, then dried over anhydrous sodium sulphate and filtered. Evaporation of the solvent left a brown oil that was chromatographed over silica gel (petroleum ether/ethyl acetate, 4:1) to give 3-methoxy-3'-(6-(trifluoromethyl)pyridin-2-yl)biphenyl-4-ol as a clear oil, 0.547 g (65%).

c) To a solution of 3-methoxy-3'-(6-(trifluoromethyl)pyridin-2-yl)biphenyl-4-ol (0.476 g, 1.38 mmol) in acetic acid (10 mL) at room temperature was added 60% nitric acid (0.12 mL, 1.52 mmol) dropwise. The resulting mixture was allowed to stir for thirty minutes then poured onto ice-water (100 mL) and the resulting precipitate was filtered off, washed with water and dried. After chromatography over silica gel (petroleum ether/ethyl acetate, 2:1), 3-methoxy-5-nitro-3'-(6-(trifluoromethyl)pyridin-2-yl)biphenyl-4-ol was obtained as a yellow solid, 0.323 g (60%).

d) To a stirred solution of 3-methoxy-5-nitro-3'-(6-(trifluoromethyl)pyridin-2-yl)biphenyl-4-ol (0.288 g, 0.738 mmol) in 1,2-dichloroethane (10 mL) cooled in an ice-water bath was added aluminium chloride (0.123 g, 0.922 mmol) in one portion followed by pyridine 0.233 g, 2.95 mmol) dropwise. The resulting red suspension was stirred at 80° C. for two hours, then cooled to room temperature and poured onto cold 2 N aqueous hydrochloric acid (100 mL). The precipitate was filtered off, washed with water and dried to give 5-nitro-3'-(6-(trifluoromethyl)pyridin-2-yl)biphenyl-3,4-diol, 0.164 g, (59%).

EXAMPLE 4

As an example of a compound of the general formula (I) having a carbonyl moiety as central unit (3,4-dihydroxy-5-nitrophenyl)(2-(trifluoromethyl)pyridin-3-yl)methanone was prepared by the following procedure:

a) To a solution of 4-benzyloxy-3-methoxy-bromobenzene (2.0 g, 6.82 mmol) in tetrahydrofuran (50 mL) at −78° C. under argon was added 2 N butyllithium solution in hexanes (3.75 mL, 7.5 mmol) dropwise. The resulting mixture was allowed to stir for one hour, whereupon a solution of N-methoxy-N-methyl-2-trifluoromethyl-nicotinamide (1.76 g, 7.5 mmol) in tetrahydrofuran (20 mL) was added dropwise. The mixture was then allowed to reach room temperature over two hours, then poured onto cold 2 N aqueous hydrochloric acid (150 mL). The mixture was extracted with diethylether, and the combined organic layers were washed with water and brine, dried over anhydrous sodium sulphate and filtered. Evaporation of the solvent left a brown oil that was chromatographed over silica gel (petroleum ether/ethyl acetate, 2:1) to give (4-benzyloxy-3-methoxy-phenyl)-(2-trifluoromethyl-pyridin-3-yl)-methanone, 1.72 g (65%).

b) To a stirred solution of (4-benzyloxy-3-methoxy-phenyl)-(2-trifluoromethyl-pyridin-3-yl)-methanone (0.913 g, 2.36 mmol) in dichloromethane cooled in an ice-water bath was added a 30% solution of hydrogen bromide in acetic acid (3.54 mL, 17.7 mmol) dropwise. The resulting solution was allowed to stir at room temperature overnight then poured onto ice-water (100 mL). The phases were separated and the aqueous phase extracted with dichloromethane (10 mL). The combined organic layers were washed with water and brine, then dried over anhydrous sodium sulphate and filtered. Evaporation of the solvent left a brown oil that was chromatographed over silica gel (petroleum ether/ethyl acetate, 1:1) to give (4-hydroxy-3-methoxyphenyl)(2-(trifluoromethyl)pyridin-3-yl)methanone as a colourless solid, 0.561 g (80%).

c) To a solution of (4-hydroxy-3-methoxyphenyl)(2-(trifluoromethyl)pyridin-3-yl)methanone (0.472 g, 1.59 mmol) in acetic acid (10 mL) at room temperature was added 60% nitric acid (0.14 mL, 1.75 mmol) dropwise. The resulting mixture was allowed to stir for thirty minutes then poured onto ice-water (100 mL) and the resulting precipitate was filtered off, washed with water and dried. Recrystallisation from ethanol afforded (4-hydroxy-3-methoxy-5-nitrophenyl)(2-(trifluoromethyl)pyridin-3-yl)methanone as a yellow solid, 0.315 g (58%).

d) To a stirred solution of (4-hydroxy-3-methoxy-5-nitrophenyl)(2-(trifluoromethyl)pyridin-3-yl)methanone (0.287 g, 0.84 mmol) in 1,2-dichloroethane (10 mL) cooled in an ice-water bath was added aluminium chloride (0.14 g, 1.05 mmol) in one portion followed by pyridine (0.26 g, 3.35 mmol) dropwise. The resulting red suspension was stirred at 80° C. for two hours, then cooled to room temperature and poured onto cold 2 N aqueous hydrochloric acid (100 mL). The precipitate was filtered off, washed with water and dried to give (3,4-dihydroxy-5-nitrophenyl)(2-(trifluoromethyl)pyridin-3-yl)methanone, 0.182 g, (66%).

EXAMPLE 5

As an example of a compound of the general formula (I) having a (Z)-1-cyanoethen-1,2-diyl moiety as central unit (Z)-3-(3,4-dihydroxy-5-nitrophenyl)-2-(6-(trifluoromethyl)pyridin-3-yl)acrylonitrile was prepared by the following procedure:

a) A suspension of vanillin (1.0 g, 6.57 mmol), 2-(6-(trifluoromethyl)pyridin-3-yl)acetonitrile (1.222 g, 6.57 mmol) and piperidine (0.71 mL, 7.23 mmol) in absolute ethanol (10 mL) was stirred at reflux for forty-eight hours and then allowed to cool to room temperature. The resulting precipitate was filtered off, washed with water and dried. Recrystallisation from isopropanol afforded (Z)-3-(4-hydroxy-3-methoxyphenyl)-2-(6-(trifluoromethyl)pyridin-3-yl)acrylonitrile as white crystals, 0.904 g (43%).

b) To a solution of (Z)-3-(4-hydroxy-3-methoxyphenyl)-2-(6-(trifluoromethyl)pyridin-3-yl)acrylonitrile (0.858 g, 2.68 mmol) in acetic acid (20 mL) was added 60% nitric acid (0.23 mL, 2.95 mmol) dropwise. The resulting mixture was allowed to stir at room temperature for thirty minutes then poured onto ice-water (100 mL). The yellow precipitate was filtered off, washed with water and dried. Recrystallisation from isopropnaol afforded (Z)-3-(4-hydroxy-3-methoxy-5-nitrophenyl)-2-(6-(trifluoromethyl)pyridin-3-yl)acrylonitrile as a yellow solid, 0.597 g, (61%).

c) To a stirred solution of (Z)-3-(4-hydroxy-3-methoxy-5-nitrophenyl)-2-(6-(trifluoromethyl)pyridin-3-yl)acrylonitrile (0.526 g, 1.44 mmol) in 1,2-dichloroethane (10 mL) cooled in an ice-water bath was added aluminium chloride (0.24 g, 1.80 mmol) in one portion followed by pyridine (0.46 g, 5.77 mmol) dropwise. The resulting red suspension was stirred at 80° C. for two hours, then cooled to room temperature and poured onto cold 2 N aqueous hydrochloric acid (100 mL). The precipitate was filtered off, washed with water and dried to give (Z)-3-(3,4-dihydroxy-5-nitrophenyl)-2-(6-(trifluoromethyl)pyridin-3-yl)acrylonitrile, 0.308 g (61%)

EXAMPLE 6

As an example of a compound of the general formula (I) having a 1H-imidazol-1,5-diyl moiety as central unit 3-nitro-5-(1-(5-(trifluoromethyl)pyridin-2-yl)-1H-imidazol-5-yl)benzene-1,2-diol was prepared by the following procedure:

a) To a stirred solution of 5-(trifluoromethyl)pyridin-2-amine (0.405 g, 2.5 mmol) in a mixture of ethanol (12.5 mL) and acetic acid (0.25 mL) at room temperature was added 3,4-dimethoxy-5-nitrobenzaldehyde (0.53 g, 2.5 mmol). The reaction was heated at reflux temperature for two hours then ethanol was evaporated. The oily residue was dissolved in a mixture of methanol (17 mL) and 1,2-dimethoxyethane (7.5 mL), whereupon 1-(isocyanomethylsulfonyl)-4-methylbenzene (TOSMIC) (0.73 g, 3.75 mmol) and potassium carbonate (0.69 g, 5 mmol) were added in one portion. The resulting mixture was stirred at reflux temperature for 3 hours. The reaction was evaporated to dryness, and then taken up in dichloromethane (50 ml). The organic phase was washed with water (50 mL) and then dried over anhydrous magnesium sulphate, filtered and evaporated to leave brown oil. Column chromatography over silica gel (petroleum ether-ethyl acetate 9:1) gave 2-(5-(3,4-dimethoxy-5-nitrophenyl)-1H-imidazol-1-yl)-5-(trifluoromethyl)pyridine, 0.542 g (55%).

b) 2-(5-(3,4-dimethoxy-5-nitrophenyl)-1H-imidazol-1-yl)-5-(trifluoromethyl)pyridine (0.394 g, 1 mmol) was heated at 140° C. in 48% aqueous hydrogen bromide (6 mL) for 2.5 hours. The dark homogeneous solution was cooled to room temperature and volatiles were removed by evaporation to leave a pale brown crystalline solid that was dried over $P_2O_5$ under vacuum. Trituration of the resulting solid with diethyl ether gave 3-nitro-5-(1-(5-(trifluoromethyl)pyridin-2-yl)-1H-imidazol-5-yl)benzene-1,2-diol as a yellow crystalline solid, 0.263 g (72%).

EXAMPLE 7

As an example of a compound of the general formula (I) having a isoxazo-3,5-diyl moiety as central unit 3-nitro-5-(4-(2-(trifluoromethyl)pyridin-3-yl)isoxazol-3-yl)benzene-1,2-diol was prepared by the following procedure:

a) To a stirred suspension of (E)-3-(3,4-dimethoxy-5-nitrophenyl)-1-(2-(trifluoromethyl)pyridin-3-yl)prop-2-en-1-one (1.146 g, 3 mmol) in ethanol (15 mL) was added 50% aqueous hydroxylamine solution (0.74 mL, 4.5 mmol) and the mixture was heated to 80° C. After stirring for 1 hour, a fine precipitate began to separate from the reaction mixture. After cooling to room temperature the yellow precipitate was filtered off, washed with ethanol and dried under vacuum to give 3-(3,4-dimethoxy-5-nitrophenyl)-4-(2-(trifluoromethyl)pyridin-3-yl)-4,5-dihydroisoxazol-5-ol, 0.904 g (73%).

b) 3-(3,4-dimethoxy-5-nitrophenyl)-4-(2-(trifluoromethyl)pyridin-3-yl)-4,5-dihydroisoxazol-5-ol (2.06 g, 5 mmol) was heated in 20 mL of ethyl acetate to 70° C. To the resulting slurry was added trifluoroacetic acid (0.74 g, 6.5 mmol) dropwise. After 10 minutes, the reaction was evaporated to dryness and the residue was recrystallised from isopropanol to give 3-(3,4-dimethoxy-5-nitrophenyl)-4-(2-(trifluoromethyl)pyridin-3-yl)isoxazole, 1.224 g (62%).

c) 3-(3,4-dimethoxy-5-nitrophenyl)-4-(2-(trifluoromethyl)pyridin-3-yl)isoxazole (0.79 g, 2 mmol) was taken up in dichloromethane (15 mL) and the yellowish suspension was cooled to −78° C. under argon whereupon boron tribromide (4.5 g, 18 mmol) was added dropwise. The reddish reaction mixture was allowed to warm to room temperature and stirred for 18 hours, then carefully poured into ice-water (100 mL) and allowed to stir for 1 hour. The yellow precipitate was filtered off, washed with water and dried over $P_2O_5$ under vacuum. Trituration with boiling ethanol gave 3-nitro-5-(4-(2-(trifluoromethyl)pyridin-3-yl)isoxazol-3-yl)benzene-1,2-diol as a yellow solid, 0.47 g (64%).

EXAMPLE 8

As an example of a compound of the general formula (I) having a furan-2,4-diyl moiety as central unit Ethyl 4-(3,4-dihydroxy-5-nitrophenyl)-2-(2-(trifluoromethyl)pyridin-3-yl)furan-3-carboxylate was prepared by the following procedure:

a) To a stirred solution of ethyl 3-oxo-3-(2-(trifluoromethyl)pyridin-3-yl)propanoate (1.305 g, 5 mmol) in pyridine (25 mL) was added 2-bromo-1-(3,4-dimethoxy-5-nitrophenyl)ethanone (1.67 g, 5.5 mmol). The reaction mixture was heated to 70° C. and stirred for 5 hours, then cooled to room temperature and poured onto 6 N aqueous HCl (100 mL). The precipitate was filtered off, washed with water and dried over $P_2O_5$ under vacuum. The solid was recrystallised from dichloromethane/ispropanol to give crude ethyl 4-(3,4-dimethoxy-5-nitrophenyl)-2-(2-(trifluoromethyl)pyridin-3-yl)furan-3-carboxylate, 1.00 g (43%).

b) 4-(3,4-dimethoxy-5-nitrophenyl)-2-(2-(trifluoromethyl)pyridin-3-yl)furan-3-carboxylate (466 mg, 1 mmol) was taken up in dichloromethane (8 mL). The yellowish suspension was cooled to −78° C. under argon and boron tribromide (0.85 mL, 9 mmol) was added dropwise. The reddish reaction mixture was allowed to warm to room temperature and stirred for 18 hours and then carefully poured into ice-water (100 mL) and stirred for 1 hour. The yellow precipitate was filtered off, washed with water and dried over $P_2O_5$ under vacuum. Recrystallisation of the solid from ethanol gave ethyl 4-(3,4-dihydroxy-5-nitrophenyl)-2-(2-(trifluoromethyl)pyridin-3-yl)furan-3-carboxylate as a yellow solid, 0.298 g (68%).

EXAMPLE 9

As an example of a compound of the general formula (I) having a oxazol-2,4-diyl moiety as central unit 3-nitro-5-(2-(2-(trifluoromethyl)pyridin-3-yl)oxazol-4-yl)benzene-1,2-diol was prepared by the following procedure:

a) To a solution of 2-(3,4-dimethoxy-5-nitrophenyl)-2-oxoethyl acetate (4.24 g, 15 mmol) in xylene (30 mL) were added 2-(trifluoromethyl)nicotinamide (3.135 g, 16.5 mmol) and boron trifluoride etherate (0.18 mL, 15 mmol). The resulting yellow solution was heated to reflux for 18 hours and then cooled to room temperature. After evaporation of the solvent, the residue was partitioned between ethyl acetate and saturated aqueous sodium bicarbonate. The organic phase was separated, washed with brine and the dried over anhydrous magnesium sulphate, filtered and evaporated. The pure 4-(3,4-dimethoxy-5-nitrophenyl)-2-(2-(trifluoromethyl)pyridin-3-yl)oxazole was obtained by column chromatography over silica gel (petroleum ether/ethylacetate 2:1) as a pale yellow solid, 2.488 g (42%).

b) 4-(3,4-dimethoxy-5-nitrophenyl)-2-(2-(trifluoromethyl)pyridin-3-yl)oxazole (1.185 g, 3 mmol) was taken up in dichloromethane (25 mL). The yellowish suspension was cooled to −78° C. under argon and boron tribromide (2.55 mL, 27 mmol) was added dropwise. The red reaction mixture was allowed to warm to room temperature and stirred for 18 hours. It was then carefully poured into ice-water (100 mL) and stirred for 1 hour. The resulting yellow precipitate was filtered off, washed with water and dried over $P_2O_5$ under vacuum. The solid was recrystallized from ethanol to give 3-nitro-5-(2-(2-(trifluoromethyl)pyridin-3-yl)oxazol-4-yl)benzene-1,2-diol as a yellow solid, 0.627 g, (57%).

EXAMPLE 10

As an example of a compound of the general formula (I) having a 1,2,4-triazin-3,5-diyl moiety as central unit 3-nitro-5-(3-(2-(trifluoromethyl)pyridin-3-yl)-1,2,4-triazin-5-yl)benzene-1,2-diol was prepared by the following procedure:

a) To a stirred solution of (Z)-2-(trifluoromethyl)nicotinohydrazonamide (1.02 g, 5 mmol) in ethanol (30 mL) was added 2-(3,4-dimethoxy-5-nitrophenyl)-2-oxoacetaldehyde (1.19 g, 5 mmol). The reaction mixture was heated to reflux for 5 hours. It was then cooled to room temperature and the solvent was removed by evaporation. The residue was dissolved in dichloromethane (30 mL) and the organic phase was washed with water and dried over anhydrous magnesium sulphate, filtered and evaporated. The crude product was recrystallized from isopropanol to give 5-(3,4-dimethoxy-5-nitrophenyl)-3-(2-(trifluoromethyl)pyridin-3-yl)-1,2,4-triazine, 1.628 g (80%).

b) 5-(3,4-dimethoxy-5-nitrophenyl)-3-(2-(trifluoromethyl)pyridin-3-yl)-1,2,4-triazine (1.221 g, 3 mmol) was taken up in dichloromethane (25 mL). The yellowish solution was cooled to −78° C. under argon and boron tribromide (2.55 mL, 27 mmol) was added dropwise. The red reaction mixture was allowed to warm to room temperature and stirred for 18 hours. It was then carefully poured into ice-water (100 mL) and stirred for 1 hour. The yellow precipitate was filtered off, washed with water and dried over $P_2O_5$ under vacuum. The solid was recrystallised from dichloromethane-ethanol to give 3-nitro-5-(3-(2-(trifluoromethyl)pyridin-3-yl)-1,2,4-triazin-5-yl)benzene-1,2-diol as a yellow solid, 0.807 g (71%).

EXAMPLE 11

As an example of a compound of the general formula (I) having a 1,3,5-triazin-2,4-diyl moiety as central unit 3-nitro-5-(4-(2-(trifluoromethyl)pyridin-3-yl)-1,3,5-triazin-2-yl)benzene-1,2-diol was prepared by the following procedure:

a) To a solution of (E)-N-((dimethylamino)methylene)-3,4-dimethoxy-5-nitrobenzamide (1.12 g, 4 mmol) ethanol (30 mL) was added 2-(trifluoromethyl)nicotinimidamide (0.756 g, 4 mmol). The reaction mixture was heated to reflux for 5 hours. It was cooled to room temperature and the solvent was removed by evaporation. The residue was then dissolved in a dichloromethane/isopropanol mixture (50 mL, 70:30) and the organic phase was washed with water, dried over anhydrous magnesium sulphate, filtered and evaporated. The crude product was recrystallized from ethanol to give 2-(3,4-dimethoxy-5-nitrophenyl)-4-(2-(trifluoromethyl)pyridin-3-yl)-1,3,5-triazine, 1.221 g (75%).

b) A portion of 2-(3,4-dimethoxy-5-nitrophenyl)-4-(2-(trifluoromethyl)pyridin-3-yl)-1,3,5-triazine (1.221 g, 3 mmol) was taken up in dichloromethane (25 mL). The yellowish solution was cooled to −78° C. under argon and boron tribromide (2.55 mL, 27 mmol) was added dropwise. The red reaction mixture was allowed to warm to room temperature and stirred for 18 hours. It was then carefully poured into ice-water (100 mL) and stirred for 1 hour. The yellow precipitate was filtered off, washed with water and dried over $P_2O_5$ under vacuum. Recrystallisation from a dichloromethane-ethanol mixture gave 3-nitro-5-(4-(2-(trifluoro-methyl)pyridin-3-yl)-1,3,5-triazin-2-yl)benzene-1,2-diol as a yellow solid, 0.966 g (85%).

EXAMPLE 12

As an example of a compound of the general formula (I) having a pyrrol-2,5-diyl moiety as central unit Ethyl 5-(3,4-dihydroxy-5-nitrophenyl)-1-methyl-2-(2-(trifluoromethyl)pyridin-3-yl)-1H-pyrrole-3-carboxylate was prepared by the following procedure:

a) To a stirred solution of methylamine (0.63 mL, 33% EtOH solution, 5 mmol) in a mixture of ethanol (25 mL) and acetic acid (0.5 mL) at room temperature was added ethyl 3-oxo-3-(2-(trifluoromethyl)pyridin-3-yl)propanoate (1.305 g, 5 mmol). The reaction mixture was heated at reflux for two hours whereupon the solvent was removed by evaporation under vacuum. To a solution of the crude product in dimethylformamide (25 mL) was added potassium carbonate (2.07 g, 15 mmol) in one portion followed by 1-(3,4-bis-benzyloxy-5-nitrophenyl)-2-bromo-ethanone (2.51 g, 5.50 mmol) and the mixture was then stirred at 100° C. Once no starting material was detectable, the reaction mixture was allowed to cool to room temperature and poured onto ice-cold 1 N aqueous hydrochloric acid (100 mL). The resulting precipitate was filtered off, washed with water and dried. The residue was chromatographed over silica gel. Homogeneous fractions were pooled and evaporated to give ethyl 5-(3,4-bis(benzyloxy)-5-nitrophenyl)-1-methyl-2-(2-(trifluoromethyl)pyridin-3-yl)-1H-pyrrole-3-carboxylate, 2.492 g (79%).

b) A solution of ethyl 5-(3,4-bis(benzyloxy)-5-nitrophenyl)-1-methyl-2-(2-(trifluoromethyl)pyridin-3-yl)-1H-pyrrole-3-carboxylate (0.189 g, 0.30 mmol) in dichloromethane (10 mL) was cooled to −78° C. with stirring and treated under argon with boron tribromide (0.30 g, 1.21 mmol). The resulting deep purple suspension was then allowed to stir at room temperature for one hour before cooling again to −78° C. The mixture was quenched by the careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give ethyl 5-(3,4-dihydroxy-5-nitrophenyl)-1-methyl-2-(2-(trifluoromethyl)pyridin-3-yl)-1H-pyrrole-3-carboxylate as a yellow solid, 0.126 g (93%).

EXAMPLE 13

As an example of a compound of the general formula (I) having a 2H-tetrazol-2,5-diyl moiety as central unit 3-nitro- 5-(2-(5-(trifluoromethyl)pyridin-2-yl)-2H-tetrazol-5-yl) benzene-1,2-diol was prepared by the following procedure:

a) A mixture of 3,4-bis-benzyloxy-5-nitro-benzonitrile (0.54 g, 1.50 mmol), sodium azide (0.15 g, 2.25 mmol) and ammonium chloride (0.12 g, 2.25 mmol) in dimethylformamide (3 mL) was stirred at 85° C. for 20 hours. After cooling to room temperature, the reaction mixture was poured onto water (30 mL) and acidified with dilute hydrochloric acid. The resulting precipitate was collected, washed with water and dried to yield 5-(3,4-bis-benzyloxy-5-nitrophenyl)-2H-tetrazole, 0.53 g (87%).

b) 2-chloro-5-(trifluoromethyl)pyridine (0.181 g, 1.00 mmol) was added to a stirred suspension of 5-(3,4-bis-benzyloxy-5-nitro-phenyl)-2H-tetrazole (0.4 g, 1.00 mmol) and potassium carbonate (0.14 g, 1 mmol) in acetonitrile (10 mL). The reaction mixture was stirred at room temperature till completion, then diluted with dichloromethane and washed with water. The organic phase was separated, dried over anhydrous magnesium sulphate, filtered and evaporated to dryness to leave a crude residue that was recrystallised from a dichloro-methane/isopropanol mixture to afford 2-(5-(3,4-bis(benzyloxy)-5-nitrophenyl)-2H-tetrazol-2-yl)-5-(trifluoromethyl)pyridine, 0.389 g (71%).

c) A solution of 2-(5-(3,4-bis(benzyloxy)-5-nitrophenyl)-2H-tetrazol-2-yl)-5-(trifluoromethyl)pyridine (0.274 g, 0.5 mmol) in dichloromethane (15 mL) was cooled to −78° C. with stirring under argon and treated with boron tribromide (1.00 g, 4.00 mmol) dropwise. The resulting deep purple suspension was then allowed to stir at room temperature for one hour before cooling again to −78° C. The mixture was quenched by the careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 3-nitro-5-(2-(5-(trifluoromethyl)pyridin-2-yl)-2H-tetrazol-5-yl)benzene-1,2-diol as a yellow solid, 0.165 g, (90%).

EXAMPLE 14

As an example of a compound of the general formula (I) having a 1,3-thiazol-2,4-diyl moiety as central unit 3-nitro-5-(2-(2-(trifluoromethyl)pyridin-3-yl)thiazol-4-yl)benzene-1,2-diol was prepared by the following procedure:

a) A mixture of 2-(trifluoromethyl)pyridine-3-carbothioamide (0.227 g, 1.10 mmol) and 1-[3,4-bis(benzyloxy)-5-nitrophenyl]-2-bromoethanone (0.50 g, 1.10 mmol) were refluxed overnight in absolute ethanol (5 mL). After cooling to room temperature, the reaction mixture was poured onto water (50 mL). The resulting precipitate was filtered off, washed with water (25 mL) and dried. Recrystallisation from dichloromethane/isopropanol afforded 4-(3,4-bis(benzyloxy)-5-nitrophenyl)-2-(2-(trifluoromethyl)pyridin-3-yl)thiazole, 0.539 g (87%).

b) A solution of 4-(3,4-bis(benzyloxy)-5-nitrophenyl)-2-(2-(trifluoromethyl)pyridin-3-yl)thiazole (0.146 g, 0.26 mmol), in dichloromethane (10 mL) was cooled to −78° C. and treated under argon, with boron tribromide (0.26 g, 1.03 mmol). The resulting deep purple suspension was then allowed to stir at room temperature for one hour before cooling again to −78° C. The mixture was quenched by careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 3-nitro-5-(2-(2-(trifluoromethyl)pyridin-3-yl)thiazol-4-yl) benzene-1,2-diol as a yellow solid, 0.087 g (87%).

EXAMPLE 15

As an example of a compound of the general formula (I) having a 1,2,4-triazol-3,5-diyl moiety as central unit 5-(4-methyl-5-(2-(trifluoromethyl)pyridin-3-yl)-4H-1,2,4-triazol-3-yl)-3-nitrobenzene-1,2-diol was prepared by the following procedure:

a) To a stirred solution of 3,4-dimethoxy-5-nitro-benzoyl chloride (0.50 g, 2.04 mmol) in dichloromethane (10 mL) at 0° C., was added dropwise methylamine (1.02 mL, 2.04 mmol, 2 M in THF). The reaction mixture was stirred at room temperature till all starting material disappeared, then diluted with dichloromethane and washed with water. The organic phase was dried over anhydrous magnesium sulphate, filtered and evaporated to dryness to leave a crude residue that was recrystallised from a dichloromethane/isopropanol mixture to afford 3,4-dimethoxy-N-methyl-5-nitro-benzamide, 0.44 g (89%).

b) To a stirred suspension of 3,4-dimethoxy-N-methyl-5-nitro-benzamide (0.40 g, 1.66 mmol) in toluene (10 mL) was added phosphorous pentachloride (0.28 g, 1.83 mmol) portionwise. Upon completion of addition, the reaction mixture was warmed to reflux till complete disappearance of starting material. Evaporation to dryness resulted in a crude solid that was washed with diethyl ether, affording 3,4-dimethoxy-N-methyl-5-nitro-benzimidoyl chloride, 0.37 g (85%).

c) A mixture of 2-(trifluoromethyl)nicotinonitrile (0.43 g, 2.50 mmol), sodium azide (0.24 g, 3.75 mmol), and ammonium chloride (0.20 g, 3.75 mmol) in dimethylformamide (2.5 mL) was stirred at 85° C. for 20 hours. After cooling to room temperature, the reaction mixture was poured onto water (20 mL) and acidified with dilute hydrochloric acid. The resulting precipitate was collected, washed with water and dried to yield 3-(2H-tetrazol-5-yl)-2-(trifluoromethyl)pyridine, 0.484 g (90%).

d) 3,4-Dimethoxy-N-methyl-5-nitro-benzimidoyl chloride (0.28 g, 1.08 mmol) was added to a stirred solution of 3-(2H-tetrazol-5-yl)-2-(trifluoromethyl)pyridine (0.215 g, 1 mmol) in dry pyridine (3 mL), preheated to 50° C. The resulting mixture was cautiously heated to 75-90° C. and maintained at this temperature until nitrogen evolution ceased. The mixture was then poured onto water (30 mL) and extracted with dichloromethane (25 mL). The organic phase was separated, dried over anhydrous magnesium sulphate, filtered and evaporated to dryness. The resulting residue was purified by chromatography to afford 3-(5-(3,4-dimethoxy-5-nitrophenyl)-4-methyl-4H-1,2,4-triazol-3-yl)-2-(trifluoromethyl)pyridine, 0.241 g (59%).

e) To a stirred suspension of 3-(5-(3,4-dimethoxy-5-nitrophenyl)-4-methyl-4H-1,2,4-triazol-3-yl)-2-(trifluoromethyl)pyridine (0.192 g, 0.47 mmol) in dichloromethane (20 mL) at −78° C. under argon was added boron tribromide (0.47 g, 1.88 mmol) dropwise. The resulting purple suspension was then allowed to stir at room temperature for seven hours before being cooled in an ice-water bath. The mixture was carefully quenched by the addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give, after drying, 5-(4-methyl-5-(2-

(trifluoromethyl)pyridin-3-yl)-4H-1,2,4-triazol-3-yl)-3-nitrobenzene-1,2-diol was obtained as an orange solid, 0.154 g (86%).

EXAMPLE 16

As an example of a compound of the general formula (I) having a 1,2,3-thiadiazol-4,5-diyl moiety as central unit 3-nitro-5-(5-(2-(trifluoromethyl)pyridin-3-yl)-1,2,3-thiadiazol-4-yl)benzene-1,2-diol was prepared by the following procedure:

a) A mixture of 1-(3,4-bis(benzyloxy)-5-nitrophenyl)-2-(2-(trifluoromethyl)pyridin-3-yl)ethanone (0.485 g, 0.93 mmol), ethyl carbazate (0.11 g, 1.06 mmol) and p-toluene sulfonic acid (4 mg) in toluene (10 mL) was refluxed until distillation of water ceased. The reaction mixture was cooled to room temperature, the solvents were evaporated to dryness, and the crude solid was triturated with diethyl ether (15 mL), filtered and dried yielding (Z)-ethyl 2-(1-(3,4-bis(benzyloxy)-5-nitrophenyl)-2-(2-(trifluoromethyl)pyridin-3-yl)ethylidene)-hydrazinecarboxylate, 0.475 g (84%).

b) A mixture of (Z)-ethyl 2-(1-(3,4-bis(benzyloxy)-5-nitrophenyl)-2-(2-(trifluoromethyl)pyridin-3-yl)ethylidene)hydrazinecarboxylate (0.388 g, 0.64 mmol), in thionyl chloride (2 mL) was refluxed until no more starting material was detected. Excess of solvent was removed and the residue was purified by chromatography over silica gel using a mixture of dichloromethane/ethanol as eluent. Homogeneous fractions were pooled and evaporated to afford 4-(3,4-bis(benzyloxy)-5-nitrophenyl)-5-(2-(trifluoromethyl)pyridin-3-yl)-1,2,3-thiadiazole, 0.184 g (51%).

c) 4-(3,4-bis(benzyloxy)-5-nitrophenyl)-5-(2-(trifluoromethyl)pyridin-3-yl)-1,2,3-thiadiazole (0.147 g, 0.26 mmol) in dichloromethane (10 mL) was cooled to −78° C. with stirring and treated under argon with boron tribromide (0.26 g, 1.03 mmol). The resulting deep purple suspension was then allowed to stir at room temperature for one hour before cooling again to −40° C. The mixture was quenched by the careful addition of methanol. After stifling at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 3-nitro-5-(5-(2-(trifluoromethyl)pyridin-3-yl)-1,2,3-thiadiazol-4-yl)benzene-1,2-diol as a yellow solid, 0.089 g (89%).

EXAMPLE 17

As an example of a compound of the general formula (I) having a 1,2,4-oxadiazol-3,5-diyl moiety as central unit 3-nitro-5-(3-(2-(trifluoromethyl)pyridin-3-yl)-1,2,4-oxadiazol-5-yl)benzene-1,2-diol was prepared by the following procedure:

a) To a stirred solution of 3,4-bis(benzyloxy)-5-nitrobenzoic acid (0.759 g, 2 mmol) in dimethylformamide (10 mL) at room temperature was added 1,1-carbonyldiimidazole (0.34 g, 2.10 mmol) in one portion. The resulting yellow mixture was allowed to stir for ninety minutes whereupon (Z)—N'-hydroxy-2-(trifluoromethyl)nicotinimidamide (0.41 g, 2 mmol) was added in one portion. The resulting mixture was stifled at room temperature for two hours and then poured onto water (100 mL). The resulting precipitate was filtered off, washed with water and dried. After recrystallisation from dichloromethane/isopropanol, (Z)—N'-(3,4-bis(benzyloxy)-5-nitrobenzoyloxy)-2-(trifluoromethyl) nicotinimidamide was obtained as a light yellow solid, 0.88 g (78%).

b) To a stirred solution of the solid obtained above (0.26 g, 0.46 mmol) in tetrahydrofuran (15 mL) at room temperature under argon was added a 1 N solution of tetrabutylammonium fluoride in tetrahydrofuran (0.7 mL, 0.7 mmol). The resulting clear yellow solution was allowed to stir at room temperature for four hours. Additional tetrabutylammonium fluoride (0.7 mmol) was added and the reaction mixture was allowed to stir for fifteen hours at room temperature and then ten hours at 55° C. After cooling to room temperature, the reaction mixture was poured onto water (150 mL). The resulting precipitate was filtered off, washed with water and dried. The crude product was chromatographed over silica gel using dichloromethane as eluent. Homogeneous fractions were pooled and evaporated to afford 5-(3,4-bis(benzyloxy)-5-nitrophenyl)-3-(2-(trifluoromethyl)pyridin-3-yl)-1,2,4-oxadiazole as an off-white solid, 0.21 g (82%).

c) A solution of 5-(3,4-bis(benzyloxy)-5-nitrophenyl)-3-(2-(trifluoromethyl)pyridin-3-yl)-1,2,4-oxadiazole (0.099 g, 0.18 mmol) in dichloromethane (5 mL) was cooled to −78° C. with stirring under argon and treated with boron tribromide (0.18 g, 0.74 mmol) dropwise. The resulting deep purple suspension was then allowed to stir at room temperature for one hour before cooling again to −78° C. The mixture was quenched by the careful addition of methanol. After stirring at room temperature for thirty minutes, the volatiles were evaporated and the residue stirred with 2 N hydrochloric acid (5 mL) for thirty minutes. The resulting solid was filtered off, washed with water (25 mL) and then cold isopropanol (5 mL) to give 3-nitro-5-(3-(2-(trifluoromethyl)pyridin-3-yl)-1,2,4-oxadiazol-5-yl)benzene-1,2-diol as a yellow solid, 0.058 g (88%).

EXAMPLE 18

As an example of a compound of the general formula (I) having a 1,2,4-oxadiazol-3,5-diyl moiety as central unit 5-[3-(2,5-dichloro-4,6-dimethylpyridin-3-yl)-[1,2,4]oxadiazol-5-yl]-3-nitrobenzene-1,2-diol was prepared by the following procedure:

a) A stirred suspension of 4-hydroxy-3-methoxy-5-nitrobenzoic acid (2.00 g, 9.38 mmol) in thionyl chloride (8.2 mL) was heated at 80° C. for two hours. The excess of thionyl chloride was removed under vacuum. The resulting yellow solid was dissolved in DMA (15.4 mL), then (Z)-2,5-dichloro-N'-hydroxy-4,6-dimethylnicotinimidamide (2.636 g, 11.26 mmol) and pyridine (6.2 mL) were added. The red solution was heated to 120° C. for 2.5 hours. The reaction mixture was cooled to room temperature and poured into a mixture of cc HCl (10 ml) and ice (80 g), then stirred for thirty minutes. The yellow precipitate was filtered off, washed with water and dried under vacuum. Recrystallization from dichloromethane-isopropanol mixture afforded 2.42 g (62%) of 4-(3-(2,5-dichloro-4,6-dimethylpyridin-3-yl)-1,2,4-oxadiazol-5-yl)-2-methoxy-6-nitrophenol as yellow crystalline.

b) To an ice-cooled solution of 4-(3-(2,5-dichloro-4,6-dimethylpyridin-3-yl)-1,2,4-oxadiazol-5-yl)-2-methoxy-6-nitrophenol (2.40 g, 5.84 mmol) in NMP (19 mL) was added aluminium chloride (0.977 g, 7.33 mmol) followed by addition of pyridine (1.93 mL). The reaction mixture was heated to 60° C. for 1 hour. It was cooled to room temperature and poured into 2 N HCl-solution (ca. 40 mL). The precipitate was filtered off, washed with water to and dried under vacuum. Recrystallization from acetic acid yielded 1.88 g (81%) of 5-[3-(2,5-dichloro-4,6-dimethylpyridin-3-yl)-[1,2,4]oxadiazol-5-yl]-3-nitrobenzene-1,2-diol.

EXAMPLE 19

Pharmaceutical formulations are prepared as follows:

Capsule:

|  |  |
|---|---|
| Compound A | 15.0% |
| Lactose monohydrate | 43.0% |
| Microcrystalline cellulose | 30.0% |
| Povidone | 4.0% |
| Croscarmellose sodium | 5.0% |
| Talc | 2.0% |
| Magnesium stearate | 1.0% |

Capsule:

|  |  |
|---|---|
| Compound A | 15.0% |
| Microcrystalline cellulose | 72.5% |
| Ethylcellulose | 5.0% |
| Sodium starch glycolate | 6.0% |
| Colloidal Silicon Dioxide | 0.5% |
| Magnesium stearate | 1.0% |

Tablet:

|  |  |
|---|---|
| Compound A | 20.0% |
| Microcrystalline cellulose | 25.0% |
| Calcium Phosphate, dibasic dihydrate | 40.0% |
| Povidone | 6.0% |
| Croscarmellose sodium | 6.0% |
| Talc | 2.0% |
| Magnesium stearate | 1.0% |

EXAMPLE 20

Patients are treated with tablets containing 50 mg of compound A to patients who are suffering from Parkinson's disease and who are on L-DOPA therapy. A significant improvement of the clinical picture is evidenced.

What is claimed is:

1. A compound or salt of formula VIA, VIB or VIC,

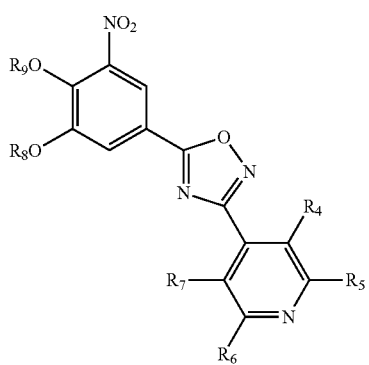

wherein $R_4$, $R_5$, $R_6$ and $R_7$ independently from each other represent hydrogen, $C_1$-$C_6$-alkyl, $C_1$-$C_6$-thioalkyl, $C_1$-$C_6$-alkoxy, $C_6$-$C_{12}$-aryloxy or a $C_6$-$C_{12}$-thioaryl group, $C_1$-$C_6$-alkanoyl or $C_7$-$C_{13}$-aroyl group, amino, $C_1$-$C_6$-alkylamino, $C_1$-$C_6$-dialkylamino, $C_3$-$C_{12}$-cycloalkylamino, $C_3$-$C_{12}$ heterocycloalkylamino, $C_1$-$C_6$-alkylsulphonyl, $C_6$-$C_{12}$-arylsulphonyl, halogen, $C_1$-$C_6$-haloalkyl, trifluoromethyl, cyano, nitro or a heteroaryl group; or two or more of residues $R_4$, $R_5$, $R_6$ and $R_7$ taken together represent aliphatic or heteroaliphatic rings or aromatic or heteroaromatic rings, wherein $R_8$ and $R_9$ each independently represent hydrogen or a protective group.

2. The compound or salt of claim 1, wherein the compound or salt is selected from 3-nitro-5-(3-(4-(trifluoromethyl)pyridin-3-yl)-1,2,4-oxadiazol-5-yl)benzene-1,2-diol, 5-(3-(2-chloro-4,6-dimethylpyridin-3-yl)-1,2,4-oxadiazol-5-yl)-3-nitrobenzene-1,2-diol, 5-(3-(2-methyl-6-(trifluoromethyl)pyridin-3-yl)-1,2,4-oxadiazol-5-yl)-3-nitrobenzene-1,2-diol, 3-nitro-5-(3-(6-(trifluoromethyl)pyridin-3-yl)-1,2,4-oxadiazol-5-yl)benzene-1,2-diol, 5-(3-(6-methyl-4-(trifluoromethyl)pyridin-3-yl)-1,2,4-oxadiazol-5-yl)-3-nitrobenzene-1,2-diol, 5-(3-(2,6-dimethyl-4-(trifluoromethyl)pyridin-3-yl)-1,2,4-oxadiazol-5-yl)-3-nitrobenzene-1,2-diol, 5-(3-(3,5-dichloropyridin-4-yl)-1,2,4-oxadiazol-5-yl)-3-nitrobenzene-1,2-diol, 5-(3-(6-methyl-2-phenyl-4-(trifluoromethyl)pyridin-3-yl)-1,2,4-oxadiazol-5-yl)-3-nitrobenzene-1,2-diol, 5-(3-(2-bromo-4,5,6-trimethylpyridin-3-yl)-1,2,4-oxadiazol-5-yl)-3-nitrobenzene-1,2-diol, 5-(3-(2-chloro-4,5,6-trimethylpyridin-3-yl)-1,2,4-oxadiazol-5-yl)-3-nitrobenzene-1,2-diol, 3-nitro-5-(3-(2-(trifluoromethyl)pyridin-3-yl)-1,2,4-oxadiazol-5-yl)benzene-1,2-diol, 5-(3-(2,5-dichloro-4,6-dimethylpyridin-3-yl)-1,2,4-oxadiazol-5-yl)-3-nitrobenzene-1,2-diol, 3-nitro-5-(3-(5-(trifluoromethyl)pyridin-3-yl)-1,2,4-oxadiazol-5-yl)benzene-1,2-diol, 5-(3-(2-fluoropyridin-3-yl)-1,2,4- oxadiazol-5-yl)-3-nitrobenzene-1,2-diol, 5-(3-(2-fluoropyridin-4-yl)-1,2,4-oxadiazol-5-yl)-3-nitrobenzene-1,2-diol, 5-(3-(6-fluoropyridin-2-yl)-1,2,4-oxadiazol-5-yl)-3-nitrobenzene-1,2-diol, 5-(3-(2-chloro-6-methylpyridin-3-yl)-1,2,4-oxadiazol-5-yl)-3-nitrobenzene-1,2-diol, 5-(3-(2-bromo-6-methylpyridin-3-yl)-1,2,4-oxadiazol-5-yl)-3-nitrobenzene-1,2-diol, 5-(3-(2-bromo-5-chloro-4,6-dimethylpyridin-3-yl)-1,2,4-oxadiazol-5-yl)-3-nitrobenzene-1,2-diol, 3-nitro-5-(5-(4-(trifluoromethyl)pyridin-3-yl)-1,2,4-oxadiazol-3-yl)benzene-1,2-diol, 5-(5-(2-chloro-4,6-dimethylpyridin-3-yl)-1,2,4-oxadiazol-3-yl)-3-nitrobenzene-1,2-diol, 5-(5-(2-methyl-6-(trifluoromethyl)pyridin-3-yl)-1,2,4-oxadiazol-3-yl)-3-nitrobenzene-1,2-diol, 3-nitro-5-(5-(6-(trifluoromethyl)pyridin-3-yl)-1,2,4-oxadiazol-3-yl)benzene-1,2-diol, 5-(5-(6-methyl-4-(trifluoromethyl)pyridin-3-yl)-1,2,4-oxadiazol-3-yl)-3-nitrobenzene-1,2-diol, 5-(5-(2,6-dimethyl-4-(trifluoromethyl)pyridin-3-yl)-1,2,4-oxadiazol-3-yl)-3-nitrobenzene-1,2-diol, 5-(5-(3,5-dichloropyridin-4-yl)-1,2,4-oxadiazol-3-yl)-3-nitrobenzene-1,2-diol, 5-(5-(6-methyl-2-phenyl-4-(trifluoromethyl)pyridin-3-yl)-1,2,4-oxadiazol-3-yl)-3-nitrobenzene-1,2-diol, 5-(5-(2-bromo-4,5,6-trimethylpyridin-3-yl)-1,2,4-oxadiazol-3-yl)-3-nitrobenzene-1,2-diol, 5-(5-(2-chloro-4,5,6-trimethylpyridin-3-yl)-1,2,4-oxadiazol-3-yl)-3-nitrobenzene-1,2-diol, 3-nitro-5-(5-(2-(trifluoromethyl)pyridin-3-yl)-1,2,4-oxadiazol-3-yl)benzene-1,2-diol, 5-(5-(2,5-dichloro-4,6-dimethylpyridin-3-yl)-1,2,4-oxadiazol-3-yl)-3-nitrobenzene-1,2-diol, 3-nitro-5-(5-(5-(trifluoromethyl)pyridin-3-yl)-1,2,4-oxadiazol-3-yl)benzene-1,2-diol, 5-(5-(2-fluoropyridin-3-yl)-1,2,4-oxadiazol-3-yl)-3-nitrobenzene-1,2-diol, 5-(5-(2-fluoropyridin-4-yl)-1,2,4-oxadiazol-3-yl)-3-nitrobenzene-1,2-diol, 5-(5-(6-fluoropyridin-2-yl)-1,2,4-oxadiazol-3-yl)-3-nitrobenzene-1,2-diol, 5-(5-(2-chloro-6-methylpyridin-3-yl)-1,2,4-oxadiazol-3-yl)-3-nitrobenzene-1,2-diol, 5-(5-(2-bromo-6-methylpyridin-3-yl)-1,2,4-oxadiazol-3-yl)-3-nitrobenzene-1,2-diol, 5-(5-(2-bromo-5-chloro-4,6-dimethylpyridin-3-yl)-1,2,4-oxadiazol-3-yl)-3-nitrobenzene-1,2-diol.

3. The compound or salt of claim 1, wherein the protective group is selected from methyl, ethyl, isopropyl, benzyl, 4-methoxybenzyl, methoxymethyl, benzyloxymethyl, methoxyethoxymethyl, tetrahydropyranyl, phenacyl, allyl, trimethylsilyl, tert-butyldimethylsilyl, benzyloxycarbonyl, tert-butoxycarbonyl, ester, sulphonate, carbamate, phophinate, acetal and ketal derivatives.

4. A compound 4-(3-(2,5-dichloro-4,6-dimethylpyridin-3-yl)-1,2,4-oxadiazol-5-yl)-2-methoxy-6-nitrophenol.

5. A pharmaceutical composition comprising a compound or salt of claim 1.

6. The pharmaceutical composition of claim 5, wherein the compound or salt is selected from 3-nitro-5-(3-(4-(trifluoromethyl)pyridin-3-yl)-1,2,4-oxadiazol-5-yl)benzene-1,2-diol, 5-(3-(2-chloro-4,6-dimethylpyridin-3-yl)-1,2,4-oxadiazol-5-yl)-3-nitrobenzene-1,2-diol, 5-(3-(2-methyl-6-(trifluoromethyl)pyridin-3-yl)-1,2,4-oxadiazol-5-yl)-3-nitrobenzene-1,2-diol, 3-nitro-5-(3-(6-(trifluoromethyl)pyridin-3-yl)-1,2,4-oxadiazol-5-yl)benzene-1,2-diol, 5-(3-(6-methyl-4-(trifluoromethyl)pyridin-3-yl)-1,2,4-oxadiazol-5-yl)-3-nitrobenzene-1,2-diol, 5-(3-(2,6-dimethyl-4-(trifluoromethyl)pyridin-3-yl)-1,2,4-oxadiazol-5-yl)-3-nitrobenzene-1,2-diol, 5-(3-(3,5-dichloropyridin-4-yl)-1,2,4-oxadiazol-5-yl)-3-nitrobenzene-1,2-diol, 5-(3-(6-methyl-2-phenyl-4-(trifluoromethyl)pyridin-3-yl)-1,2,4-oxadiazol-5-yl)-3-nitrobenzene-1,2-diol, 5-(3-(2-bromo-4,5,6-trimethylpyridin-3-yl)-1,2,4-oxadiazol-5-yl)-3-nitrobenzene-1,2-diol, 5-(3-(2-chloro-4,5,6-trimethylpyridin-3-yl)-1,2,4-oxadiazol-5-yl)-3-nitrobenzene-1,2-diol, 3-nitro-5-(3-(2-(trifluoromethyl)pyridin-3-yl)-1,2,4-oxadiazol-5-yl)benzene-1,2-diol, 5-(3-(2,5-dichloro-4,6-dimethylpyridin-3-yl)-1,2,4-oxadiazol-5-yl)-3-nitrobenzene-1,2-diol, 3-nitro-5-(3-(5-(trifluoromethyl)pyridin-3-yl)-1,2,4-oxadiazol-5-yl)benzene-1,2-diol, 5-(3-(2-fluoropyridin-3-yl)-1,2,4-oxadiazol-5-yl)-3-nitrobenzene-1,2-diol, 5-(3-(2-fluoropyridin-4-yl)-1,2,4-oxadiazol-5-yl)-3-nitrobenzene-1,2-diol, 5-(3-(6-fluoropyridin-2-yl)-1,2,4-oxadiazol-5-yl)-3-nitrobenzene-1,2-diol, 5-(3-(2-chloro-6-methylpyridin-3-yl)-1,2,4-oxadiazol-5-yl)-3-nitrobenzene-1,2-diol, 5-(3-(2-bromo-6-methylpyridin-3-yl)-1,2,4-oxadiazol-5-yl)-3-nitrobenzene-1,2-diol, 5-(3-(2-bromo-5-chloro-4,6-dimethylpyridin-3-yl)-1,2,4-oxadiazol-5-yl)-3-nitrobenzene-1,2-diol, 3-nitro-5-(5-(4-(trifluoromethyl)pyridin-3-yl)-1,2,4-oxadiazol-3-yl)benzene-1,2-diol, 5-(5-(2-chloro-4,6-dimethylpyridin-3-yl)-1,2,4-oxadiazol-3-yl)-3-nitrobenzene-1,2-diol, 5-(5-(2-methyl-6-(trifluoromethyl)pyridin-3-yl)-1,2,4-oxadiazol-3-yl)-3-nitrobenzene-1,2-diol, 3-nitro-5-(5-(6-(trifluoromethyl)pyridin-3-yl)-1,2,4-oxadiazol-3-yl)benzene-1,2-diol, 5-(5-(6-methyl-4-(trifluoromethyl)pyridin-3-yl)-1,2,4-oxadiazol-3-yl)-3-nitrobenzene-1,2-diol, 5-(5-(2,6-dimethyl-4-(trifluoromethyl)pyridin-3-yl)-1,2,4-oxadiazol-3-yl)-3-nitrobenzene-1,2-diol, 5-(5-(3,5-dichloropyridin-4-yl)-1,2,4-oxadiazol-3-yl)-3-nitrobenzene-1,2-diol, 5-(5-(6-methyl-2-phenyl-4-(trifluoromethyl)pyridin-3-yl)-1,2,4-oxadiazol-3-yl)-3-nitrobenzene-1,2-diol, 5-(5-(2-bromo-4,5,6-trimethylpyridin-3-yl)-1,2,4-oxadiazol-3-yl)-3-nitrobenzene-1,2-diol, 5-(5-(2-chloro-4,5,6-trimethylpyridin-3-yl)-1,2,4-oxadiazol-3-yl)-3-nitrobenzene-1,2-diol, 3-nitro-5-(5-(2-(trifluoromethyl)pyridin-3-yl)-1,2,4-oxadiazol-3-yl)benzene-1,2-diol, 5-(5-(2,5-dichloro-4,6-dimethylpyridin-3-yl)-1,2,4-oxadiazol-3-yl)-3-nitrobenzene-1,2-diol, 3-nitro-5-(5-(5-(trifluoromethyl)pyridin-3-yl)-1,2,4-oxadiazol-3-yl)benzene-1,2-diol, 5-(5-(2-fluoropyridin-3-yl)-1,2,4-oxadiazol-3-yl)-3-nitrobenzene-1,2-diol, 5-(5-(2-fluoropyridin-4-yl)-1,2,4-oxadiazol-3-yl)-3-nitrobenzene-1,2-diol, 5-(5-(6-fluoropyridin-2-yl)-1,2,4-oxadiazol-3-yl)-3-nitrobenzene-1,2-diol, 5-(5-(2-chloro-6-methylpyridin-3-yl)-1,2,4-oxadiazol-3-yl)-3-nitrobenzene-1,2-diol, 5-(5-(2-bromo-6-methylpyridin-3-yl)-1,2,4-oxadiazol-3-yl)-3-nitrobenzene-1,2-diol, 5-(5-(2-bromo-5-chloro-4,6-dimethylpyridin-3-yl)-1,2,4-oxadiazol-3-yl)-3-nitrobenzene-1,2-diol.

7. The pharmaceutical composition as claimed in claim 5, wherein the protective group is selected from methyl, ethyl, isopropyl, benzyl, 4-methoxybenzyl, methoxymethyl, benzyloxymethyl, methoxyethoxymethyl, tetrahydropyranyl, phenacyl, allyl, trimethylsilyl, tert-butyldimethylsilyl, benzyloxycarbonyl, tert-butoxycarbonyl, ester, sulphonate, carbamate, phophinate, acetal and ketal derivatives.

8. The pharmaceutical composition as claimed in claim 5, further comprising L-DOPA and/or an aromatic L-amino acid decarboxylase inhibitor.

9. The pharmaceutical composition as claimed in claim 8, wherein the aromatic L-amino acid decarboxylase inhibitor is benserazide or carbidopa.

10. A method of treating a central and peripheral nervous system disorder, comprising the step of administering to the subject a compound or salt of claim 1.

11. The method of claim 10, wherein the central and peripheral nervous system disorder is movement disorder, a gastrointestinal disturbance, an oedema formation state or hypertension.

12. The method of claim 11, wherein the movement disorder is Parkinson's disease.

13. The method of claim 11, wherein the movement disorder is restless legs syndrome.

14. The method of claim 11, wherein the central and peripheral nervous system disorder is an oedema formation state or hypertension.

\* \* \* \* \*